United States Patent
Brydon

(10) Patent No.: US 6,547,743 B2
(45) Date of Patent: Apr. 15, 2003

(54) RESPIRATORY-ANALYSIS SYSTEMS

(75) Inventor: John William Ernest Brydon, Waverton (AU)

(73) Assignee: ResMed Limited, North Ryde (AU)

(*) Notice: Subject to any disclaimer, the term of this patent is extended or adjusted under 35 U.S.C. 154(b) by 0 days.

(21) Appl. No.: 09/423,951
(22) PCT Filed: May 18, 1998
(86) PCT No.: PCT/AU98/00358
§ 371 (c)(1), (2), (4) Date: Apr. 20, 2000
(87) PCT Pub. No.: WO98/52467
PCT Pub. Date: Nov. 26, 1998

(65) Prior Publication Data
US 2003/0045806 A1 Mar. 6, 2003

(30) Foreign Application Priority Data
May 16, 1997 (AU) ............................................. PO6855
Jul. 24, 1997 (AU) ............................................. PO8204
Dec. 16, 1997 (AU) ............................................. PP0956

(51) Int. Cl.$^7$ ................................................ A61B 5/08
(52) U.S. Cl. ...................................... 600/534; 600/529
(58) Field of Search ................................. 600/534, 529

(56) References Cited

U.S. PATENT DOCUMENTS

| | | | |
|---|---|---|---|
| 4,320,766 A | | 3/1982 | Alihanka et al. |
| 4,686,999 A | * | 8/1987 | Snyder et al. ............... 128/716 |
| 5,448,996 A | | 9/1995 | Bellin et al. |
| 5,479,932 A | | 1/1996 | Higgins et al. |
| 5,515,865 A | * | 5/1996 | Scanlon ....................... 128/721 |
| 5,522,382 A | * | 6/1996 | Sullivan et al. .......... 128/204.23 |

FOREIGN PATENT DOCUMENTS

| | | | |
|---|---|---|---|
| DE | 35 31 399 | 3/1986 | |
| EP | 0020110 A1 | 12/1980 | |
| EP | 0514744 A1 | 11/1992 | |
| FR | 1354865 | 5/1974 | |
| FR | 2 742 648 | 6/1997 | |
| GB | 2166871 A * | 5/1986 | ............ A61B/5/08 |
| GB | 2 192 460 | 1/1988 | |
| GB | 2261290 | 5/1993 | |
| GB | 2166871 A * | 5/1996 | ............ A61B/5/08 |
| JP | 1572425 | 7/1980 | |
| WO | WO 86/05965 A1 | 10/1986 | |
| WO | WO 91/19456 | 12/1991 | |
| WO | WO 94/14374 A1 | 7/1994 | |
| WO | WO 96/36279 A1 | 11/1996 | |

OTHER PUBLICATIONS

J. Siivola, "New Noninvasive Piezoelectric Transducer for Recording of Respiration, Heart Rate and Body Movements," *Medical & Biological Engineering & Computing*, Jul. 1989, pp. 423–424.

AMP "Piezo Film Sensors Techinical Manual," Dec. 1993, pp. iii–v, 1–79.

O. Polo Partial Upper Airway Obstruction During Sleep- -Studies with Static Charge-Sensitive Bed (SCSB), Acta Physiologica Scandanavica, vol. 145, Supplement 606, Helsinki 1992, pp. 11–118.

* cited by examiner

Primary Examiner—Robert L. Nasser
Assistant Examiner—Patricia Mallari
(74) Attorney, Agent, or Firm—Pillsbury Winthrop LLP

(57) ABSTRACT

A movement sensitive mattress has a plurality of independent, like movement sensors for measuring movement at different locations on the mattress to generate a plurality of independent movement signals. The signals are processed to derive respiratory variables including rate, phase, maximum effort or heart rate. Such variables can be combined to derive one or more diagnostic variables including apnea and labored breathing classifications.

39 Claims, 33 Drawing Sheets

RESPIRATORY-ANALYSIS SYSTEMS

FIELD OF THE INVENTION

The invention relates to respiratory-analysis mattresses and systems, and to methods of use thereof.

The invention further relates to the measurement of respiratory, cardiac and other movement related functions in patients suffering from a range of respiratory syndromes, including the disordered breathing associated with Cheyne Stokes syndrome, anaesthetic induced partial respiratory obstruction and sleep apnea.

BACKGROUND OF THE INVENTION

Sleep apnea is a respiratory syndrome known to be present in about 8% of the adult male human population and 4% of the adult female human population.

The syndrome manifests itself as the repetitive cessation of, or large reduction in, breathing while the patient is asleep—respectively termed apneas and hypopneas. Apneas may be divided further into central apneas, where the cause of the apnea is the failure of the nervous system to activate the muscles responsible for respiration, and obstructive apneas, where the patient tries to breath but is prevented from doing so by the temporary collapse on inspiration of his or her upper airway. The reasons for such collapses are not completely understood but may include a loss of tone in those muscles which hold the airway open plus an anatomical disposition towards a narrow upper airway.

Prior to treatment the syndrome must be diagnosed. Conventionally, this is performed by an overnight study in a specialised sleep clinic, connecting the patient to electrophysical and respiratory measurement equipment to monitor physiological variables such as the electroencephalogram, blood oxygen saturation, heartrate, chest wall movement, and respiratory air flow during the various stages of sleep.

The attachment of the such monitoring equipment requires skilled staff and is often disruptive to the patient's sleep. Furthermore, the recording of all the physiological variables requires considerable computing power and the subsequent analysis, although assisted by computer, still requires considerable attention by the staff.

Monitoring of the patient's sleep in the patient's home traditionally uses a simplified form of the above-mentioned equipment which still may be complex and disruptive to the patient's sleep.

The measurement of less disruptive variables which correlate well with the traditional ones has been pursued as a way of making such sleep studies simpler to perform and less disruptive to the patient.

A device used in this area is the Static Charge Sensitive Bed (SCSB) described in U.S. Pat. No. 4,320,766 (Allihanka et al). U.S. Pat. No. 4,320,766 describes a mattress which outputs a single electrical signal that varies with the patient's movement. By suitable electrical filtering of the movement signal indications of body movement, respiration, snore and heartbeat are produced for subsequent display.

The SCSB principle was extended by Crawford and Kennard in their published UK patent application, GB 2 166 871 A (1984), for a Respiration Monitor. Here, strips of polyvinylidene fluoride (PVDF) were assembled in a common, parallel connection in order to give area coverage of a patient's respiratory movement. PVDF is a piezoelectric plastics material readily available in strips and sheets of minimal thickness.

A PVDF sensor has also been used in a device described by Siivola [Siivola J., (1989) New noninvasive piezoelectric transducer for recording of respiration, heart rate and body movements. *Med. & Biol Eng. & Comput.* 27, 423–424].

The clinical use of the SCSB is extensively described in the PhD thesis of Dr O. Polo (Dept of Physiology, University of Turku, Finland) republished as a supplement in *Acta Physiologica Scandinavica* Vol 145, Supplementum 606, 1992.

A PVDF film based device for detecting and recording snoring is also described in International Publication No. WO 96/36279 (Sullivan).

A limitation of the SCSB is that because of its inherent planar construction it cannot be used to localise the source of the movement it detects. Likewise, the above-mentioned devices also generate minimal spatial information. A major consequence of this is that the outputs of the said devices vary considerably with patient orientation. This limits the accuracy of information that can be derived from them.

DISCLOSURE OF THE INVENTION

The invention seeks to provide a respiratory-analysis mattress and system and associated method which overcome or at least ameliorates some of the deficiencies of the prior art.

According to the invention there is provided a mattress for monitoring patient movement for a patient lying on the mattress, the mattress including at least a plurality of independent like movement sensors for measuring movement at different locations on the mattress to generate a plurality of independent movement signals.

Preferably, the respiratory-analysis mattress includes the range three to ten such movement sensors.

Preferably, the movement sensors are formed by piezoelectric elements, for example polyvinylidene fluoride (PVDF) sensor strips.

Conveniently, at least some of said piezoelectric elements are arranged to measure lateral strain across the mattress, and preferably substantially parallel to each other.

In one embodiment of the invention, the mattress comprises a compressible filling surrounded by an outer (not necessarily outermost) layer, and the piezoelectric elements are attached, preferably by adhesive, to an inside surface of the outer layer.

Alternatively, the elements are laminated between two thin conformable elastic sheets.

In another embodiment of the invention the mattress takes the form of a thin movement-sensitive sheet, in which each piezoelectric element is enclosed within a waterproof envelope of material.

Such a movement-sensitive sheet can be mounted on a carrier sheet adapted to be placed over a conventional mattress.

Conveniently, each piezoelectric element is connected to a separate transition connector, which may for example be a printed circuit board (PCB), in such a manner as to avoid strain between the element and the transition connector during use of the mattress.

Alternatively, the piezoelectric elements can be connected to a single bus transition connector, which may for example be a single bus board.

In a further embodiment of the invention, said piezoelectric elements are integrally formed from a single composite sheet of piezoelectric material.

The piezoelectric material may be PVDF.

In this case, the piezoelectric elements can be formed by forming a series of staggered parallel cuts in a sheet of piezoelectric material, in such a way that each piezoelectric elements is formed between two adjacent such cuts, and folding each piezoelectric element through an angle so that the piezoelectric elements become spaced from each other, while remaining integrally connected together by a connecting portion of said sheet of piezoelectric material.

Conveniently, said angle is substantially 90°.

In one embodiment, a strengthening portion of said sheet of piezoelectric material is folded, and attached to, said piezoelectric elements in order to hold the strips in position.

Preferably, each piezoelectric element is provided with upper and lower metallised surface layers which are arranged not to overlap on the folded portion of the element, thus ensuring that any strain on the folded portion of the element does not contribute to the electrical signal produced by the element.

The invention also provides a respiratory-analysis system comprising a mattress as described above connected to processing means for receiving and processing said movement signals to derive said respiratory variable(s). The diagnostic variables can include respiratory rate, respiratory phase, respiratory effort and maximum respiratory rate.

Preferably, the output signals from each movement sensor are separately and independently processed. The resulting processed information may subsequently be combined by the computing means during further processing.

Preferably, each piezoelectric strip is connected to the computing means via a sensor buffer comprising an operational amplifier operating as a charge amplifier, wherein the input of the operational amplifier is protected against high voltage transients, which may be produced by the piezoelectric strip, by means of a resistor connected in parallel across the two inputs of the operational amplifier, said resistor having an impedance which is large compared with the input impedance of the virtual earth of the charge amplifier.

In addition a further resistor, having an impedance which is small compared to the output impedance of the piezoelectric strip, can be placed in series with the input of the operational amplifier.

Alternatively, two diodes can be connected in parallel, and in opposite directions, across the two inputs of the operational amplifier in order to limit the maximum voltage applied to the inputs of the operational amplifier.

The invention further provides that the processing means combined one or more of said respiratory variables to give one or more derived diagnostic variables.

The derived variables can include apnea classification, snore or obstructed breathing.

The invention further provides a method for monitoring patient movement for a patient lying on a mattress, the method comprising the steps of: measuring displacement due to body movement at a plurality of independent positions length-wise of a portion of the body to derive independent signals representative of respective individual body displacement at said positions.

The invention yet further provides a method for monitoring at least one respiratory variable for a patient lying on a mattress, the method comprising the steps of: measuring displacement due to body movement at a plurality of independent positions length-wise of a portion of the body to derive independent signals representative of respective individual body displacement at said positions; and processing said movement signals to derive said respiratory variable(s).

The invention yet further provides a respiratory analysis system for monitoring at least one respiratory variable for a patient, comprising: input means to receive a plurality of signals indicative of patient movement; and processor means to process said receive signals to derive said respiratory variable(s).

The invention further provides the method may further comprise detecting the occurrence of non-respiratory sudden body movements by at least detecting high frequency components of the movement signals in the absence of diagnostic signals indicating obstructive or central apnea occurrence.

The method may further comprise determining the degree of obstructed breathing present by at least detecting the ratio of respiratory effort signal to respiratory displacement signal plus optionally the amplitude of the snore signal.

The method may further comprise controlling the output treatment pressure of a Continuous Positive Accuracy Pressure (CPAP) treatment machine on the basis of information obtained in preceding steps of the method.

Such control either occurs in real-time, that is as the respiration is being monitored, or retrospectively, where accumulated respiratory data is processed to determine the treatment pressure subsequently to be programmed into the CPAP machine.

The method may further comprise storing video information relating to the patient only for those periods during which an apnea has been detected as explained above.

The method may further comprise outputting any of the information obtained in preceding steps of the method to a display or printer, or to an analogue physiological input channel of a polygraph in such a way as to display information in alphanumeric form on the display of the polygraph.

BRIEF DESCRIPTION OF THE INVENTION

A number of embodiments of the invention will now be described, by way of example only, with reference to the accompanying drawings, in which:

FIG. 12b is a cross-section taken along A—A' in FIG. 12a;

DESCRIPTION OF PREFERRED EMBODIMENTS

Figure 1:
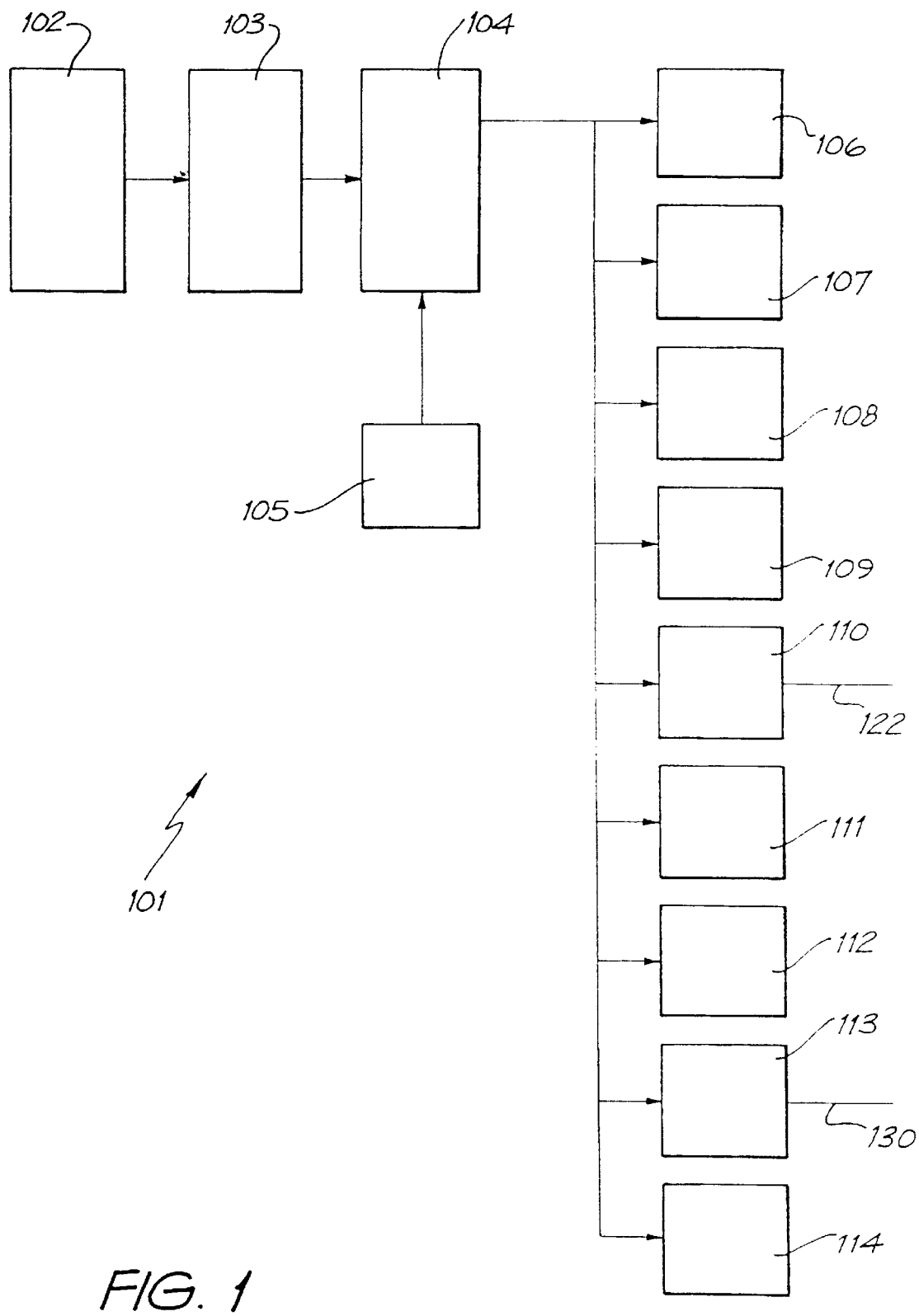
FIG. 1 is a schematic overview of a respiratory-analysis system to be described below.

FIG. 1 gives an overview of a system 101 which measures the body movements of a reclining person and from those measurements determines parameters of his or her respiratory, cardiac and other movement-related functions. The aforesaid parameters can be used to diagnose a range of respiratory disorders, in particular those associated with sleep apnea. The system can be used both in a hospital and in a patient's home.

The system 101 comprises sensor means 102 which generates electrical signals in response to movement of a reclining person, interface means 103 which converts the said signals into a form that can be processed by the computing means 104 (FIG. 1). The computing means 104 processes the said signals to produce the above-mentioned respiratory and movement parameters which are then further combined to produce parameters diagnostic of respiratory disorders associated with various types of sleep apnea. The function of the computing means 104 is determined by the control means 105, which is operated by medical staff who are directing the use of the system.

The aforesaid processing can be in real time, that is at the same time as the said signals are being recorded, or in a review process where the said recorded signals are recalled from storage and processed at some time after their acquisition.

Some or all of the diagnostic parameters can then be displayed using a display means 106, recorded for subsequent review on computer disk by a recording means 107, printed using a printing means 108, transmitted to another location using a transmission means 109 and output to a recording polygraph by polygraph input means 110. Additionally, if a particular preset condition of the diagnostic parameters is met a video camera 111 can be switched on to record moving or stationary video images of the patient's body position and movements. Alternatively, or optionally, a similar or different preset condition can activate an alarm means 112 to indicate to another person the occurrence of the said preset condition. An external Constant Positive Airway Pressure (CPAP) flow generator may optionally be controlled via CPAP control means 113. Sound output means 114 may be used to listen to snore signals, either in real time or on subsequent replay of data.

The system can operate both in a real time mode, producing diagnostic parameters in immediate response to signals from the sensor means 102 or in a retrospective mode wherein the said signals are replayed from a computer disk and diagnostic parameters calculated at the time of replay.

Figure 2A:
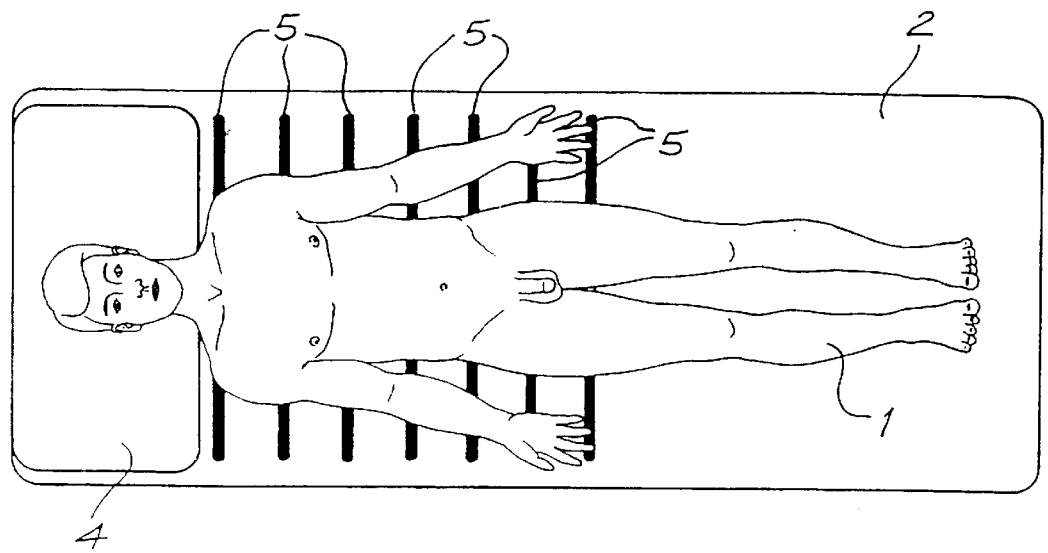
FIGS. 2a and 2b are respectively plan and side views of a movement-sensitive mattress forming part of the system.
Figure 2B:
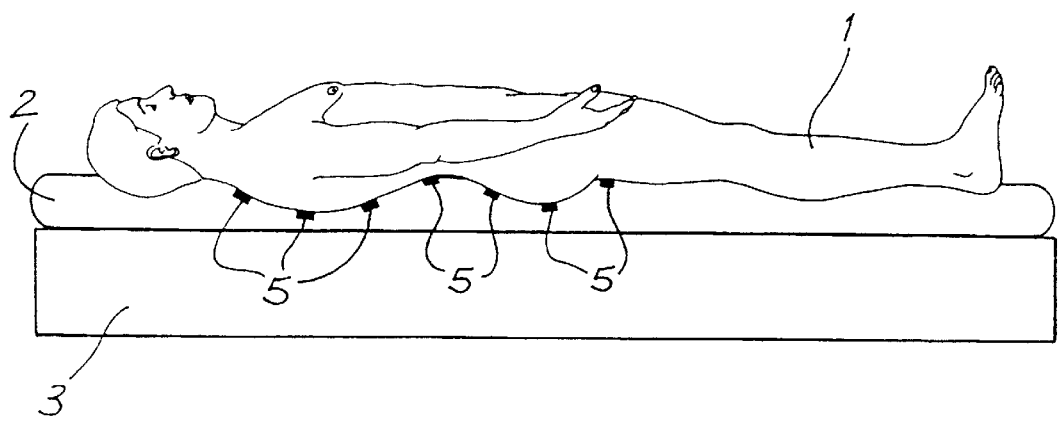

Referring to FIGS. 2a and 2b, sensor means 102 comprises a movement-sensitive mattress 2 which can rest on top of a conventional mattress 3 on which the patient 1 lies. FIG. 2b shows the movement-sensitive mattress 2 above the conventional mattress 3, but this could alternatively be below the conventional mattress 3. The patient's head may optionally rest on a pillow 4.

Figure 3:
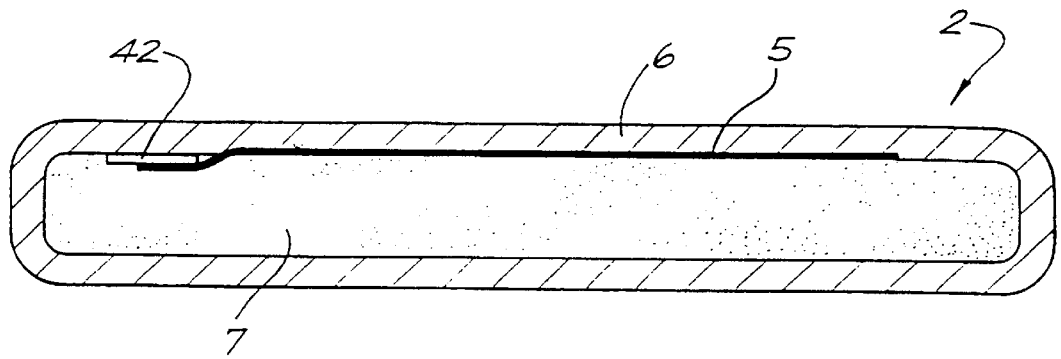
FIG. 3 is a cross-sectional view through the movement-sensitive mattress.

As shown in FIG. 3, movement-sensitive mattress 2 comprises a sandwich of low density polyethylene foam 7 enclosed by a neoprene envelope 6 constructed in such a way that movements of the patient's body cause stretching of the neoprene envelope 6.

Figure 4A:
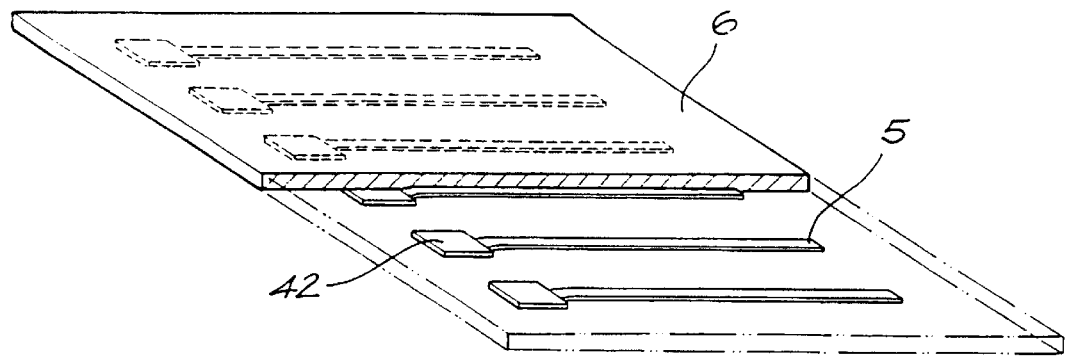
FIG. 4a is a cut-away schematic drawing of the movement-sensitive mattress showing the internal sensor strips.

Referring to FIG. 4a, affixed to the inside surface of the top side of the neoprene envelope 6 are a number of sensor strips 5, arranged in one or more patterns that span most of the patient's body. The patterns may run laterally across the movement-sensitive mattress as illustrated, or vertically from head to toe, or a combination or superposition of both. Electrical signals are conducted from the sensor strips 5 by sensor strip connectors 42.

At a minimum, three sensor strips 5 arranged to be level with the patient's rib cage area are required to obtain useful electrical signals utilised for subsequent processing. A typical range is between three and ten sensors.

Figure 4B:
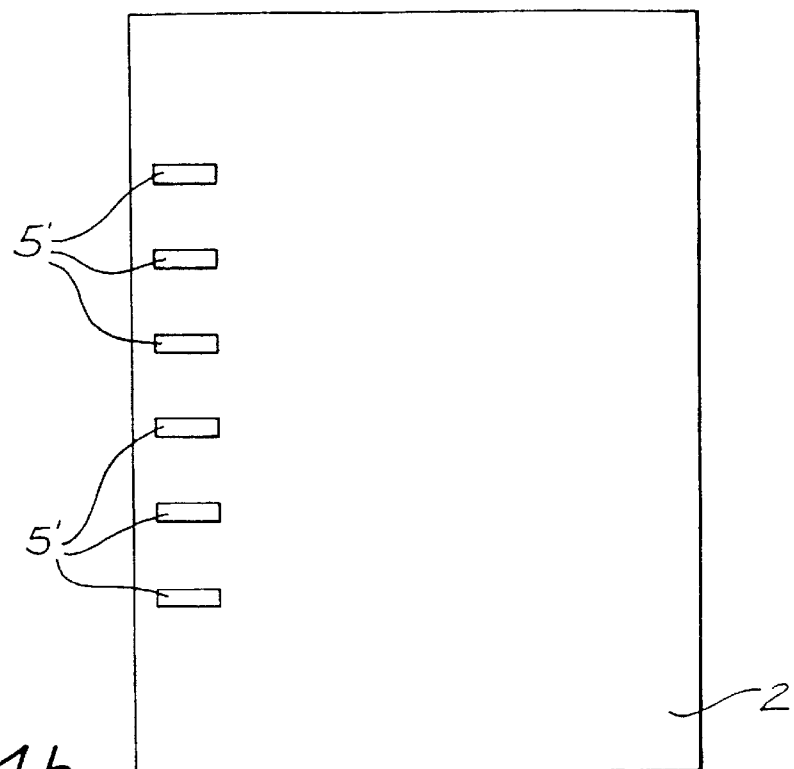
FIGS. 4b and 4c are top views of further embodiments of movement-sensitive mattresses.

In FIG. 4b, six sensor strips 5' are arranged in a spaced-apart configuration. The sensor strips are formed in the same manner as those shown in FIG. 4a, however are substantially shorter than the width of the mattress 2. A signal is taken off from each sensor strip 5'. In the limiting case the signals act as spot strain gauges.

Figure 4C:
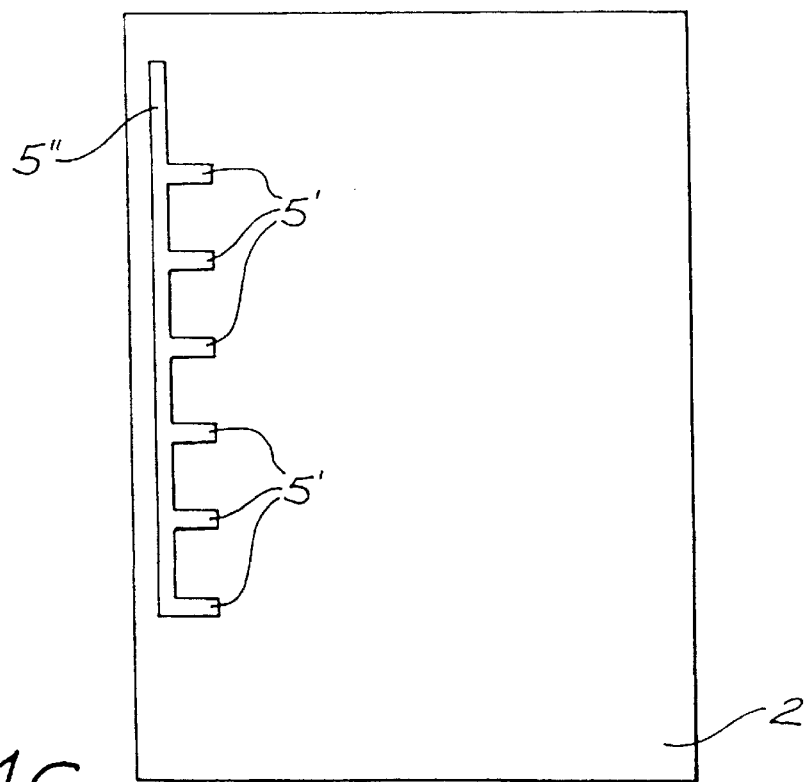

In FIG. 4c, the same sensor strips 5' are connected to a common bus connector 5a that provides for individual take-off points for each sensor strip.

Figure 5:
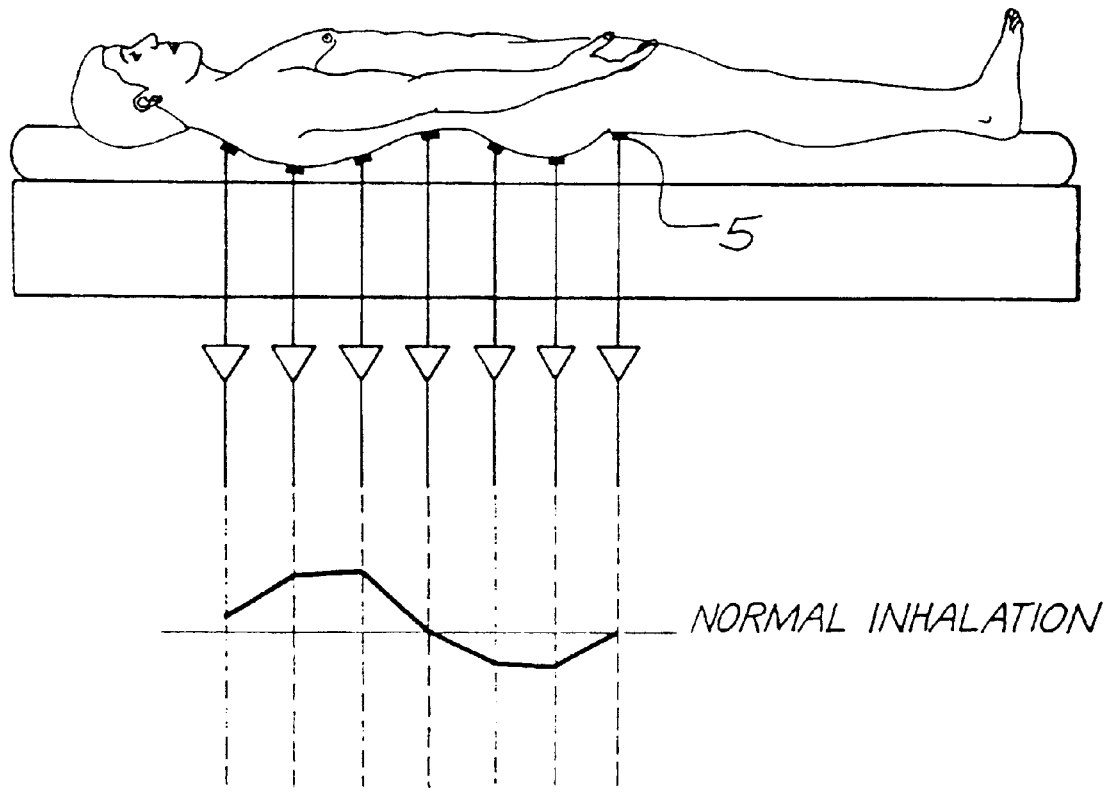
FIG. 5 illustrates the use of the movement-sensitive mattress to produce a multichannel electrical signal indicating the displacement of the patient's body near the sensor strips.

By the above means a multichannel electrical signal is derived, the channels of which reflect the localised displacement of the patient's body in the vicinity of each of the sensor strips 5, as indicated in FIG. 5. By this means the movement of the body during, for example, respiration may be monitored. This, therefore, provides a means of imaging the displacements of the torso, particularly with regard to respiration, in a reclining patient. By virtue of its many sensor strips, the system is largely insensitive to patient orientation on the movement-sensitive mattress 2.

Figure 6:
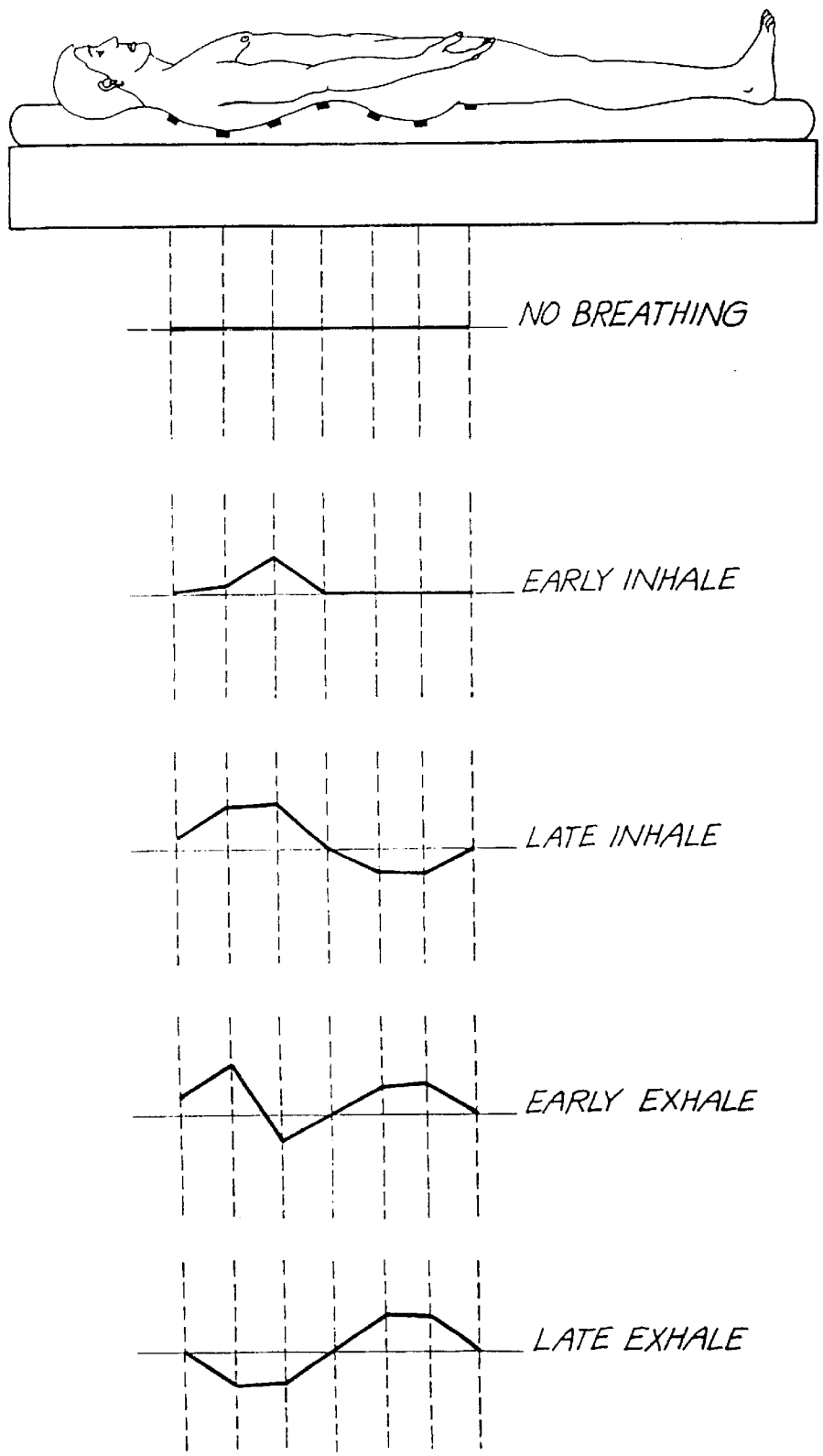
FIG. 6 illustrates a sequence of displacements of the patient's body associated with normal breathing.
Figure 7:
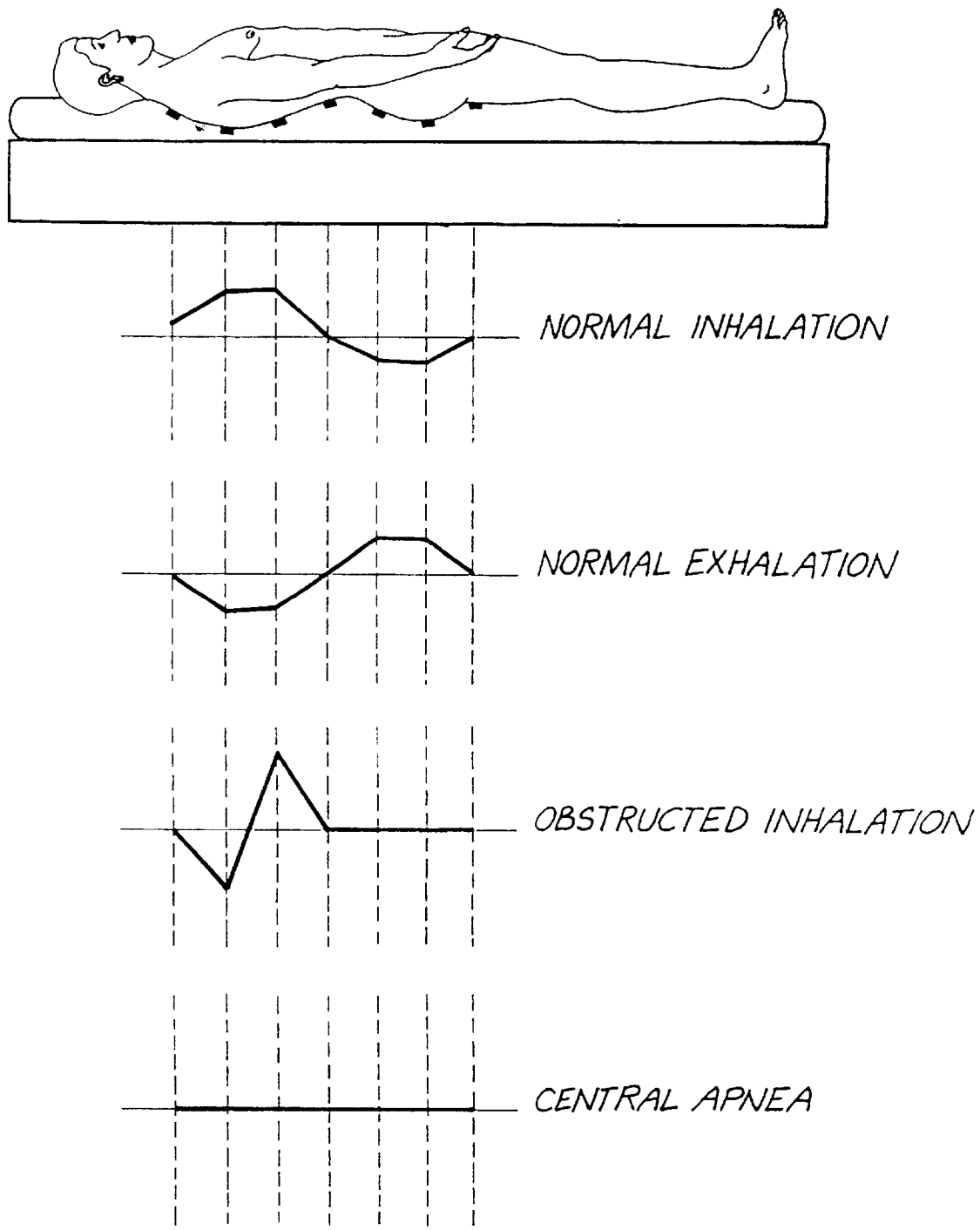
FIG. 7 illustrates a sequence of displacements of the patient's body associated with disordered breathing.

Different respiratory states of the patient produce different patterns of the aforementioned displacements. FIG. 6 illustrates typical patterns during normal respiration while FIG. 7 illustrates typical patterns associated with disordered breathing.

Figure 8A:
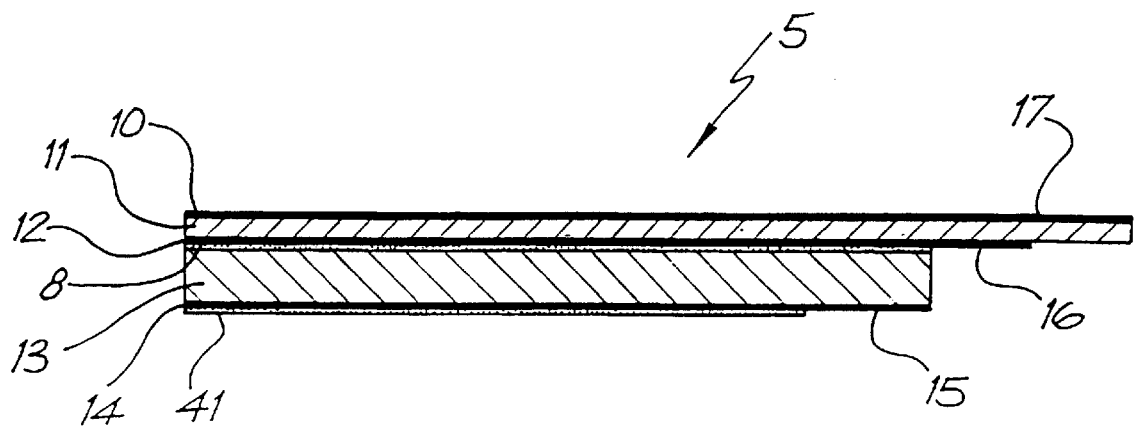
FIGS. 8a and 8b are respectively schematic cross-sectional and plan views of one of the sensor strips.
Figure 8B:
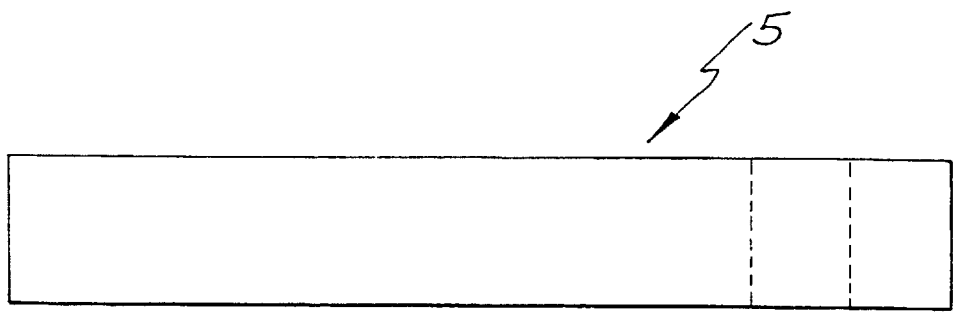

Referring to FIG. 8a, the sensor strips 5 are constructed of a layer of polyvinyledene fluoride (PVDF) film 11, a supporting mylar film 13, an adhesive layer 8 to join together the said films and an adhesive layer 41 to adhere the resulting assembly to the inside surface of the neoprene envelope 6, as shown in FIG. 3.

The PVDF film 11 has the property whereby an electrical charge is generated across the faces of the film 11 when a mechanical strain is applied along the length of the film 11 The electrical charge is conducted from the surface of the layer PVDF film 11 by two conductive, metallised surface layers, a first layer 10 and the second layer 12 which are affixed to opposing faces of the film 11 during its manufacture.

The mylar film 13 acts as a physical support for the PVDF film 11 and regulates the amount of strain applied to the said film when the sensor strip 5 is stretched. The mylar film 13 also has applied on one face a conductive, metallised surface layer 14 which is used to screen the second conductive layer 12 of the PVDF film 11 from external electrical interference. The first conductive layer 10 of the said PVDF film 11 is externally connected to the metallised layer 14 of the mylar film 13 so that the second conductive layer 12 of PVDF film 11 is effectively screened on both sides from electrical interference.

Typical dimensions of each sensor strip 5 are 650 mm long by 12 mm wide. The PVDF film is typically 28 $\mu$m in thickness and the mylar film 13 typically 1 mil in thickness. The sensor strip 5 can, for example, be made up from the above-mentioned films by the AMP Corporation of PO Box 799, Valley Forge, Pa. 19482, USA, as a modification of their standard range of piezoelectric film products.

Figure 9A:
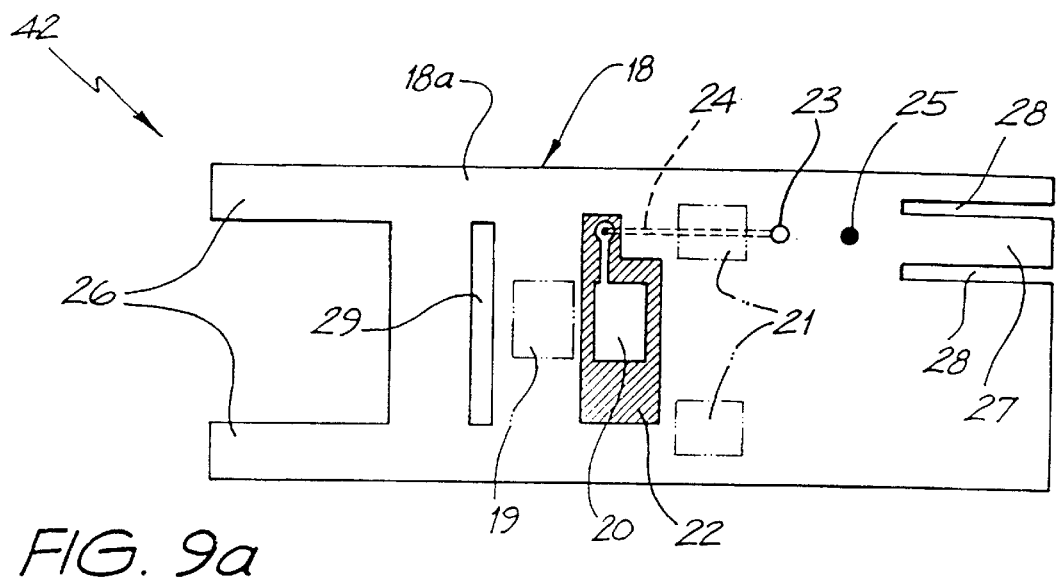
FIGS. 9a and 9b show the connection means of a sensor strip respectively before and after connection of the sensor strip thereto.
Figure 9B:
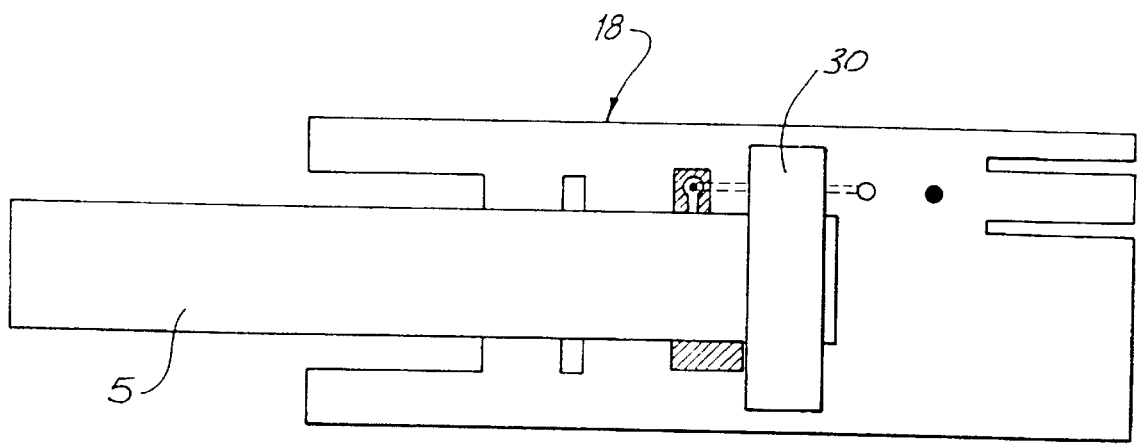

Referring to FIGS. 9a and 9b, electrical charge generated by each of the sensor strips 5 is conducted from the sensor strip 5 by a sensor strip connection means 42. The connection means 42 makes connections to the first conductive layer 10 and second conductive layer 12 of the PVDF film 11 and the metallised layer 14 of the mylar film 13, and, further, electrically connects first conductive layer 10 and metallised layer 14 together for electrical screening purposes. The resultant two electrical paths are connected to a coaxial cable 33 for transmission to interface means 103.

As shown in FIG. 8a, the various layers at one end of the sensor strip 5 are staggered in such a way as to provide conductive areas 15 and 16 which will be described below. Sensor strip connection means 42 (see FIG. 9a) comprises a double sided printed circuit board 18 with a contact area 19 that makes electrical contact via conductive adhesive with a conductive area 15 (see FIG. 8a) of the metallised layer 14 of the mylar film 13; a contact area 20 that makes electrical contact with a conductive area 16 of the second conductive layer 12 of the PVDF film 11; and a contact area 21 that makes electrical contact with the first conductive layer 10 of the PVDF film 11 by means of a conducting bridge 30 described below. Most of the surface 18a of the printed circuit board 18 adjacent to the aforesaid electrical contacts to sensor strip 5 is unetched, that is, it remains as conductive copper. This allows the electrical connection between the metallised layer 14 of the mylar film 13 and the first conductive layer 10 of the PVDF film 11, both of which are subsequently grounded. Contact area 20 is electrically isolated from said conductive copper by an etched insulating area 22. This allows contact with the ungrounded second conductive layer 12 of the PVDF film 11.

The electrical signal from the conductive area 16 of second conductive face 12 of PVDF film 11, connected to sensor strip connection means 42 via contact area 20 is conducted from the said contact area to connecting pad 23 via copper track 24 located on the reverse side of printed circuit board 18.

As shown in FIG. 9b, the electrical signal from first conductive layer 10 of PVDF film 11 is connected to the conducting copper top face of contact area 21 of printed circuit board 18 by a conducting bridge 30 constructed from copper tape with conductive adhesive on its contact side. The electrical signal from the conducting copper top face of printed circuit board 18 is conducted to a connecting pad 25 on the printed circuit board 18.

Figure 10A:
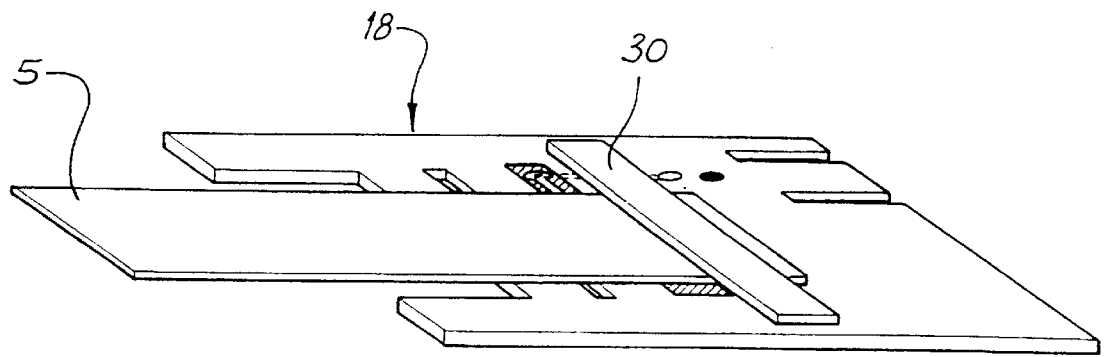
FIGS. 10a and 10b show the connection means with the sensor strip attached, but respectively before and after attachment of a rigid pressure plate.
Figure 10B:
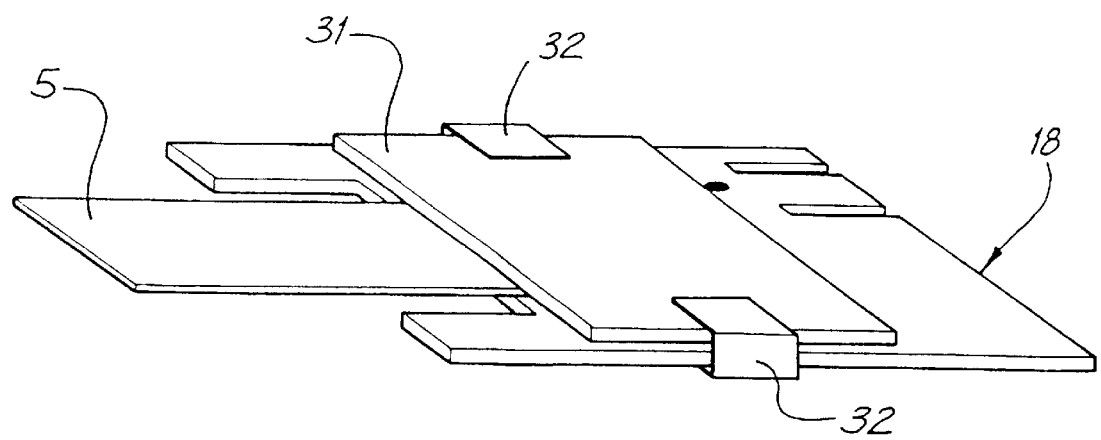

As shown in FIG. 10b, conducting bridge 30 and the two other aforementioned sensor strip connections are maintained in a state of intimate connection with their respective contact areas 19, 20, 21 by a non-conducting, rigid pressure plate 31 which bears down on the aforementioned contact assemblies by virtue of two pressure springs 32.

Figure 11A:
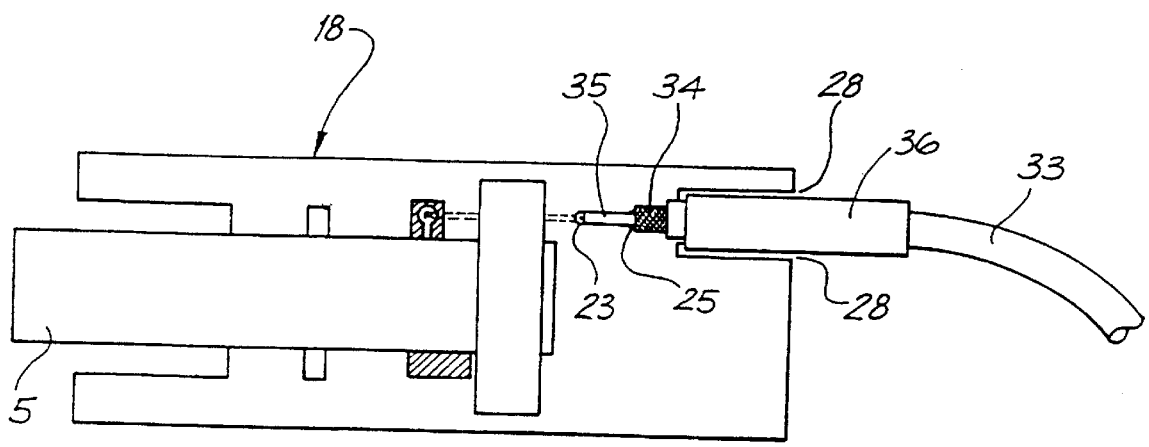
FIGS. 11a and 11b show the connection of a coaxial cable to the connection means.

Referring to FIG. 11a, to a connecting pad 23 on the printed circuit board 18 is soldered or otherwise electrically attached the inner conductor 35 of a coaxial cable 33. To connecting pad 25 is soldered or otherwise electrically attached the outer screening conductor 34 of the coaxial cable 33.

Figure 11B:
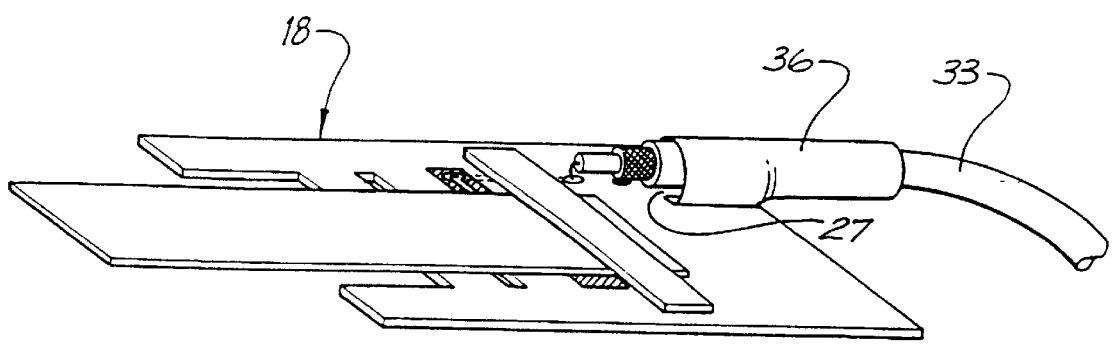

The coaxial cable 33 is attached to circuit board 18 by a method which simultaneously stress relieves the soldered connections and locates the cable 33. The coaxial cable 33 is located over cable location tongue 27 (as illustrated in FIGS. 11a & 11b), sourced from circuit board 18 by two parallel slots 28. This arrangement allows a heatshrink sleeve 36 to be pushed simultaneously over the coaxial cable 33 and the cable location tongue 27 so that, on the application of heat, the reduction in diameter of the heatshrink sleeve 36 pulls the coaxial cable 33 into intimate and stable contact with the cable location tongue 27. Adhesive on the interior of the heatshrink sleeve 36 plus its physical grip when shrunk ensure that the coaxial cable 33 is clamped sufficiently for there to be no strain on its internal conductors 34 and 35.

Figure 12A:
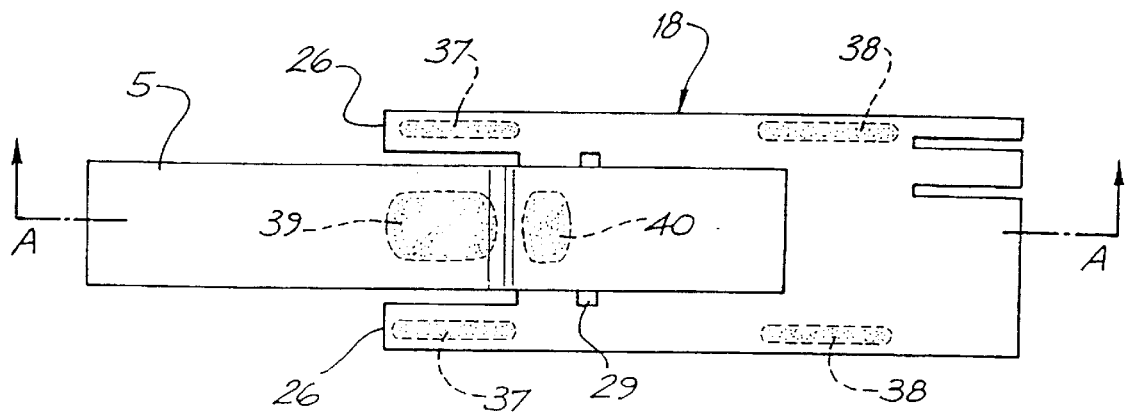
FIG. 12a shows the attachment of the sensor strip to the connection means.
Figure 12B:
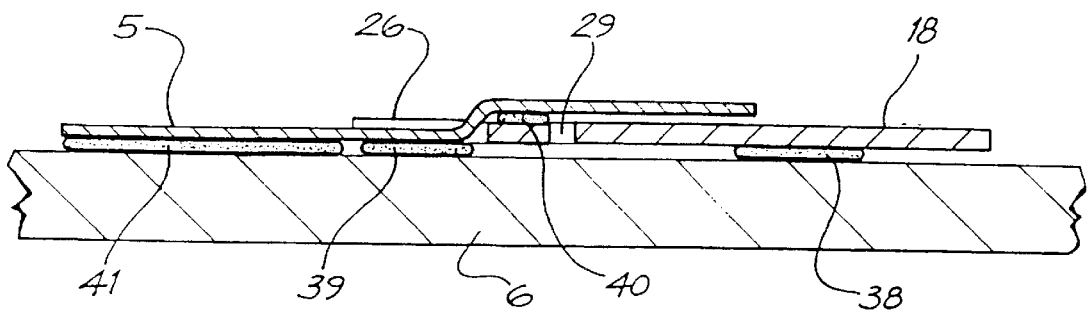

Referring to FIGS. 12a and 12b, the circuit board 18 is attached to the interior of the neoprene envelope 6 using a novel arrangement of adhesive that reduces the strain on the electrical connections between the sensor strip 5 and the circuit board 18. The sensor strip 5 is attached to the circuit board 18 using adhesive in location 40; adhesive barrier slot 29 is cut in the circuit board to prevent adhesive from location 40 straying into contact area 19. Adhesives in the location 40 and subsequently described are all of a high strength cyano-acrylic gel type such as that sold under the registered trademark "LOCITE 454". The sensor strip 5 is attached to the neoprene envelope 6 along its length by an adhesive strip 41, for example the transfer adhesive sold under the registered trademark "3M TYPE 9460".

The circuit board 18 is constructed with two strain relief horns 26 which are attached to the interior surface of the neoprene envelope 6 using the above-mentioned cyano-acrylic adhesive applied at locations 37. The function of the strain relief horns 26 is to limit the stretch of the neoprene envelope 6 in the vicinity of the attachment of the circuit board 18 to the sensor strip 5 thus significantly reducing the strain on the aforementioned electrical connections with the strip 5. Optionally, the sensor strip 5 can additionally be stabilised by the application of the said cyanoacrylic adhesive at location 39. The remainder of circuit board 18 is attached to the neoprene envelope 6 using said cyano-acrylic adhesive in at least locations 38.

Figure 13:
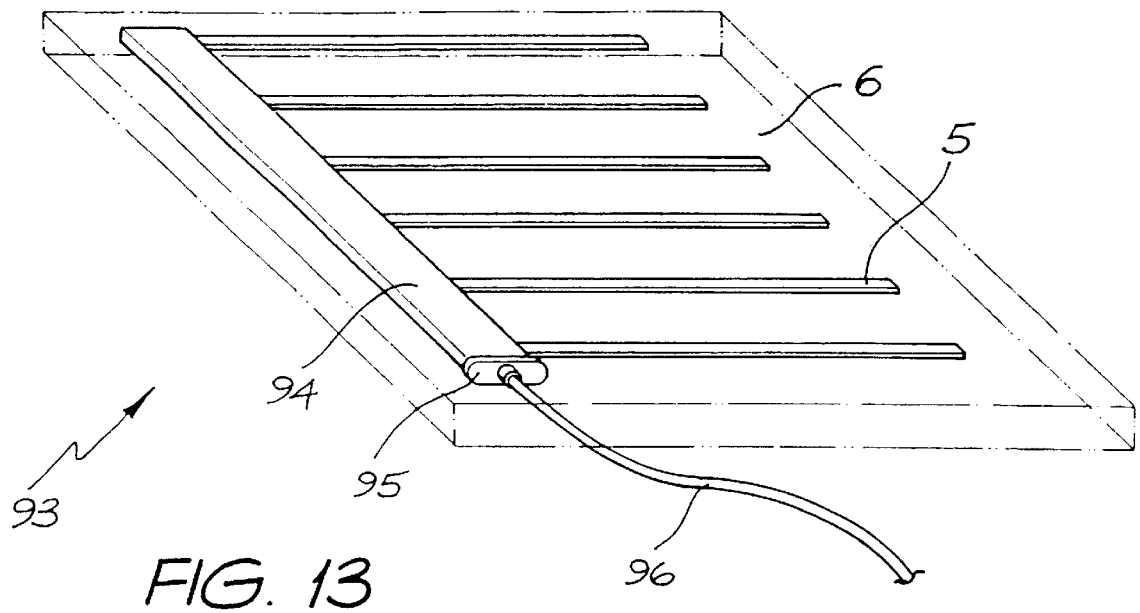
FIG. 13 shows an alternative embodiment in which the sensor strips are connected to a single bus board instead of to individual circuit boards.

Referring to FIG. 13, an alternative embodiment 93 combines circuit boards 18 in parallel on to one long bus board 94 or circuit strip such that the individual connections to strips 5 are conducted in parallel to a single multichannel connector 95 to which is connected a single multicore cable 96 which conducts all the signals from sensor strips 5. Optionally, sensor buffers 43 described below may be located in close proximity to the bus board 94.

Figure 14A:
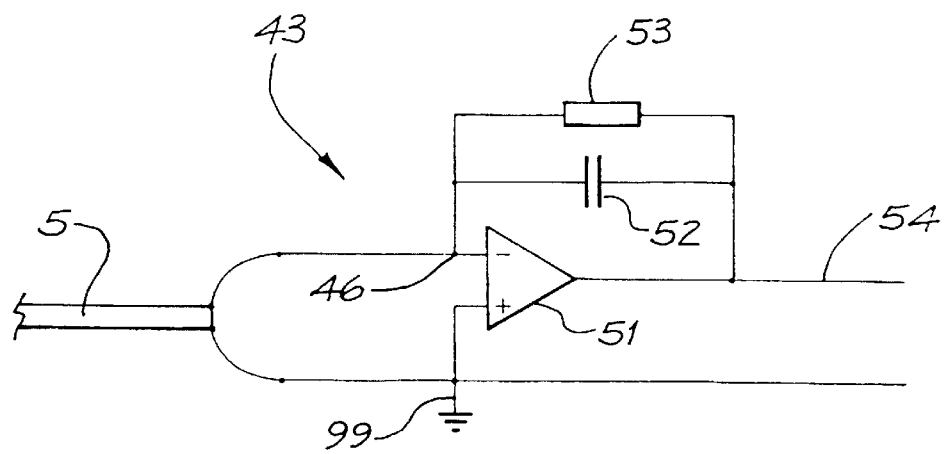
FIGS. 14a to 14d show the connection of the sensor strip (via the coaxial cable shown in FIGS. 11a and 11b, but omitted from FIGS. 14a to 14d) to four alternative embodiments of sensor buffers.
Figure 14B:
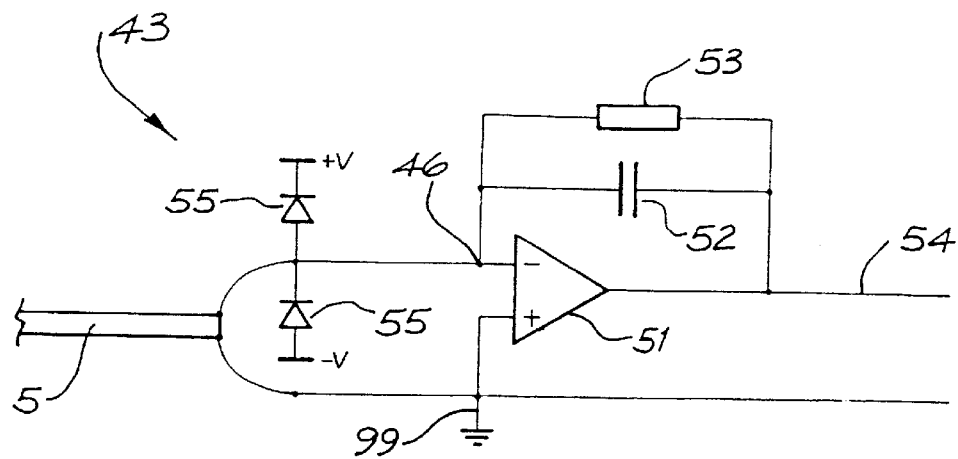

Referring to FIGS. 14a to 14d, electrical signals from each sensor strip connection means 42 are conducted to a respective sensor buffer 43 via the coaxial cable 33 (not shown in FIGS. 14a to 14b). The sensor buffer 43 can be of the form where an operational amplifier 51 operates as a charge amplifier (as shown in FIG. 14a). balancing charge received from sensor strip 5 in response to the patient's movement, against charge built up on a capacitor 52 from operational amplifier output 54. This design is commonly used in such situations and referenced in "Piezo Film Sensors Technical Manual O/N: 6571" published by the AMP Corporation of PO Box 799, Valley Forge, Pa. 19482, USA. This Technical Manual also indicates the necessity of using silicon diodes 55 (as shown in FIG. 14b) to protect the input of the operational amplifier 51 against high voltage transients produced if sensor strip 5 is subjected to a large impulsive force. The action of the diodes 55 is to clamp the input voltage of the operational amplifier 51 to approximately the operational amplifier supply voltages, +V and -V as indicated in the FIG. 14b.

The use of the protection diodes 55 in the above-mentioned configuration does however have a drawback, namely the reverse leakage current of the diodes 55 flows into the virtual earth 46 of the operational amplifier 51 which results in a compensating offset voltage at the output 54 of the operational amplifier 51.

Figure 14C:
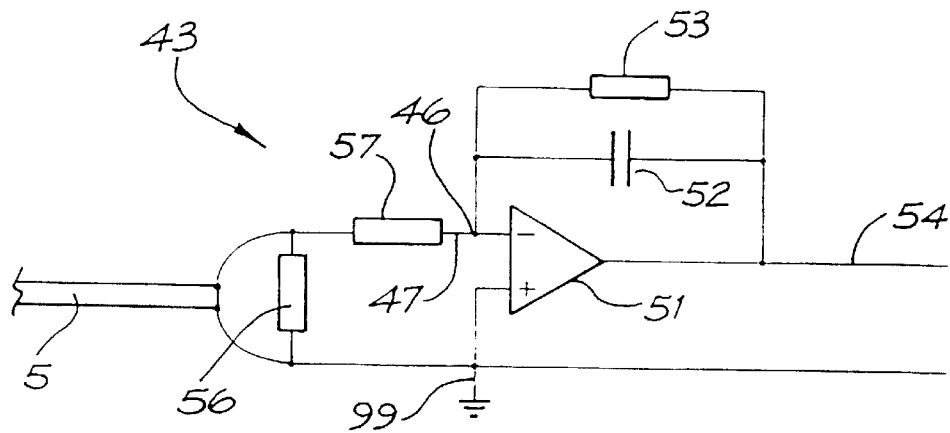
Figure 14D:
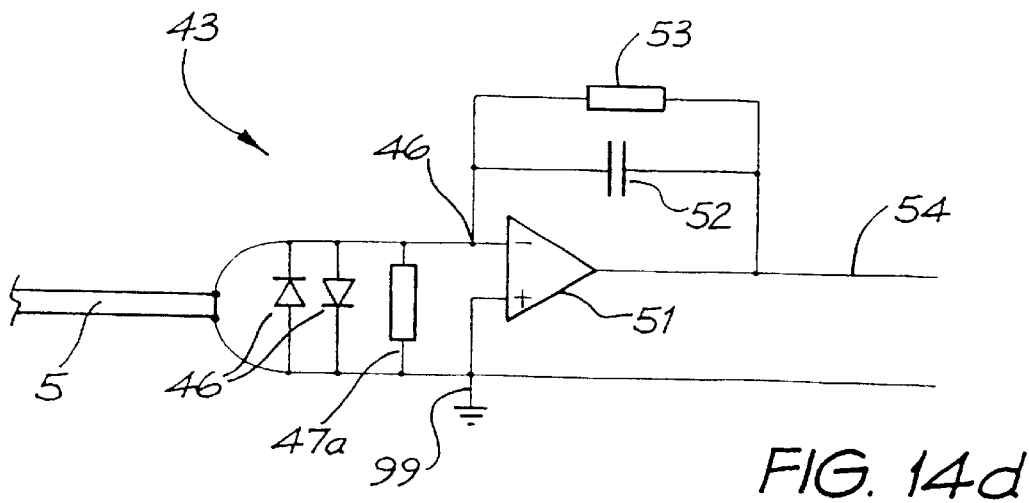

Two solutions to this problem are presented, and shown in FIGS. 14c and 14d respectively. The input 47 of the sensor strip 5 to the operational amplifier 51 in the above-mentioned charge amplifier configuration is a virtual earth 46, that is the negative feedback of the operational amplifier 51 acts to maintain the voltage at the input 47 at zero. In practice the input voltage at input 47 may be a small number of millivolts because of constructional imperfections within the operational amplifier 51. Notwithstanding this latter voltage, the input impedance of such a virtual earth is very low (because the operational amplifier acts to drain away charge in order to maintain the virtual earth)—some tens of ohms at the most, therefore an external impedance can be placed between the virtual earth point 46 and ground 99 and, providing said impedance is larger than about 1000 ohms, that is, large relative to the virtual earth impedance, the functioning of the charge amplifier is unaffected. This allows a combination of parallel 56 and serial 57 impedances to replace the above-mentioned reverse biased diodes 55 connecting the virtual earth 46 to the above-mentioned operational amplifier supply rails (±V). Whereas the voltage on the sensor strip 5 produced by the accumulation of charge due to a large impulsive force applied thereto may be large—of the order of 100 volts—the effective source impedance of the sensor strip 5 is also very large—up to $10^{12}$ ohms. Hence the addition of even a fairly large impedance (by electronic standards) of 1 Mohm across the sensor strip 5 dramatically reduces the open circuit voltage that can occur across the strip 5. As an additional precaution, a small series resistor 57 can be placed in series with the output of the sensor strip 5 to limit any residual current flow into the operational amplifier 51 input under overload conditions. During non-overload operation these components are effectively invisible to the charge amplifier function—parallel resistor 56 is much greater than the input impedance of the above-mentioned virtual earth and series resistor 57, which is typically 1 kohm, is effectively zero compared with the $10^{12}$ ohms source impedance of the sensor strip 5. One additional advantage of this configuration is that parallel resistor 56 supplies bias current to the operational amplifier 47 input, thus relieving DC feedback stabilisation resistor 53 of any magnitude constraints (in the above-mentioned conventional charge amplifier, feedback resistor 53 is limited in magnitude because increasing its value increases the output offset voltage of the amplifier).

As an alternative to the above embodiment of FIG. 14c, silicon diodes 46 can be used back to back between the virtual earth 46 and ground 99 (as shown in FIG. 14d). Under non-overload conditions the voltage across the diodes 46 is insufficient for them to conduct, hence they are invisible to the charge amplifier circuit. Under overload conditions one of the diodes 46 will conduct if the voltage increases above about 0.5 volts, thus limiting the overload voltage applied to the input 47 of operational amplifier 51. Optionally, a parallel resistor 47a of about 1 Mohm can be placed in parallel with the diodes 46 to provide bias current for the operational amplifier inputs, thereby relieving the above-mentioned magnitude constraint on DC feedback resistor 53.

DC feedback stabilisation resistor 53 in conjunction with feedback capacitor 52 forms a highpass filter with an effective—3 dB frequency of approximately 0.1 Hz. Signal components below this value, being largely due to thermoelectric and slow semiconductor drift effects are, therefore, attenuated. This technique is referenced in the aforementioned "Piezo Film Sensors Technical Manual O/N: 6571"

The outputs 54 of the charge amplifiers 43 are then passed through a further gain stage 44 (see FIG. 15) which comprises a low pass filter with a −3 dB frequency point of approximately 100 Hz.

Figure 15:
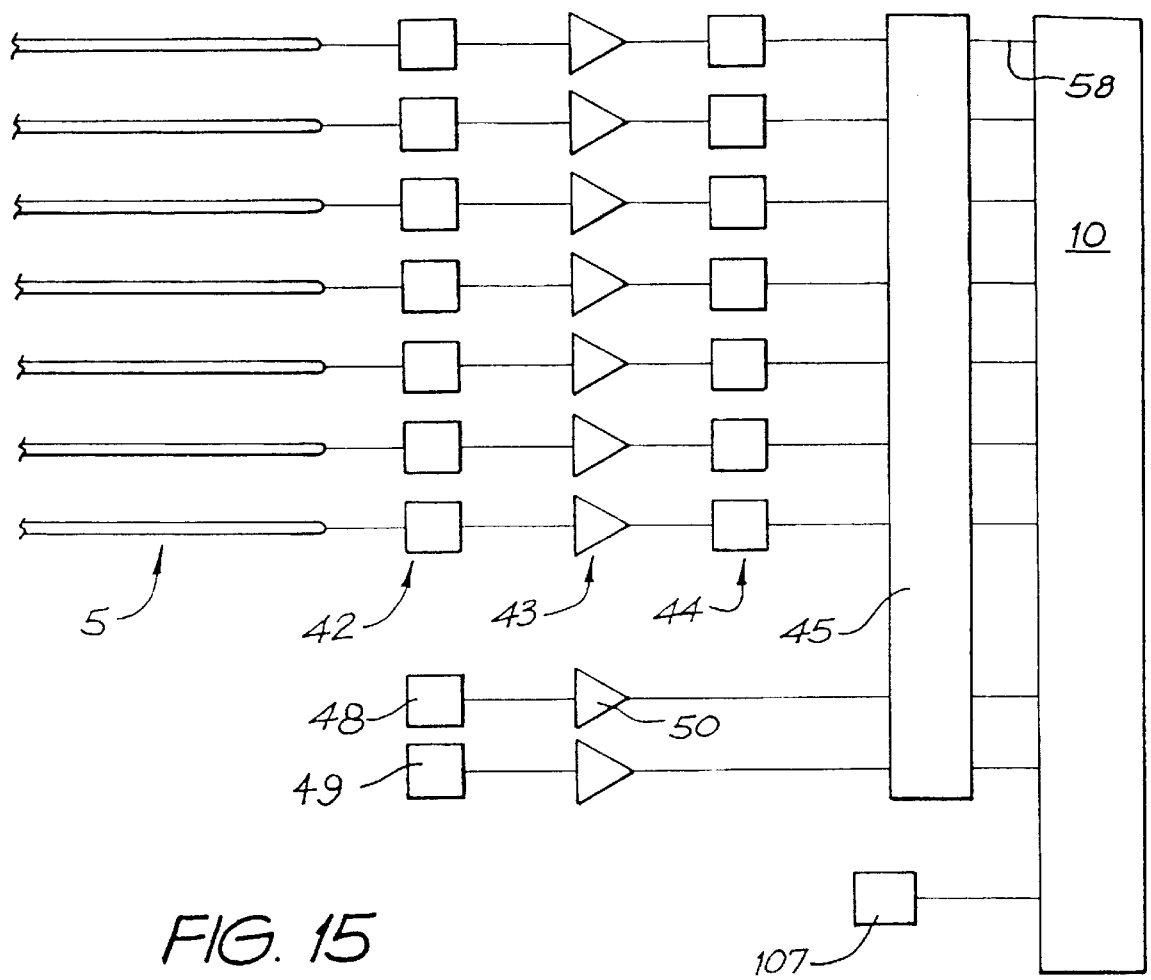
FIG. 15 shows the connection of the sensor strips to computing means via strip connection means, sensor buffers, gain stages, and an analog to digital converter.

Referring to FIG. 15, the outputs of gain stages 44 are input to a multichannel Analog to Digital Converter (ADC) 45 which has at least as many inputs as there are sensor strips 5. The ADC converter 45 transforms each of the inputs to a numerical digital signal 58 for subsequent processing and storage with a precision of at least 12 bits at a rate of approximately 200 samples per second.

The digital output signals 58 of the ADC 45 are input to computing means 104 which processes the inputs and which stores the digital outputs to computer disk 107 for subsequent retrieval.

Optionally one or more external electrical inputs 48,49 are provided to permit the recording and subsequent processing of signals derived from the movement-sensitive mattress 2. Such signals are, typically, the output from an oximeter (not shown) attached to the finger or ear of the patient, and the output from a pressure transducer (not shown) connected to a mask on the patient's face or nasal prongs inserted in the patient's nares in order to detect respiration.

External electrical inputs 48,49 are connected to combination buffer amplifiers and low pass filters 50 the outputs of which are connected to the inputs of the ADC 45 in parallel with the above-mentioned sensor strip gain stages 44 for similar conversion to digital outputs 45 but at sampling rates typically lower, say at 50 Hz.

Figure 16:
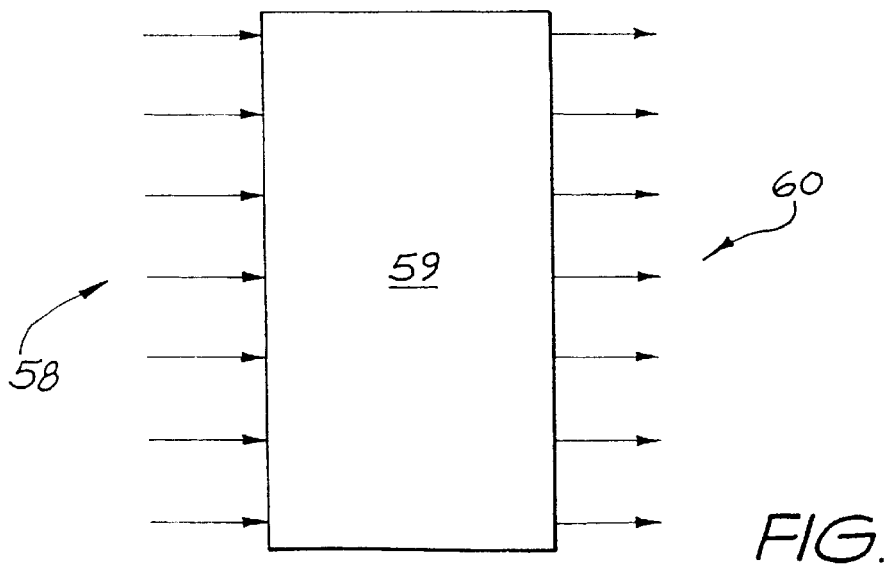
FIG. 16 shows pre-processing means for deconvolving input digital signals to produce output pre-processed digital signals.

Referring to FIG. 16, digitised signals 58 resulting from movements of the sensor strips 5 in the movement-sensitive mattress 2 are input to pre-processing means 59 (forming part of the computing means 104) to produce pre-processed digitised signals 60. The pre-processing means 59 acts both temporally on each individual channel of the digitised signals and spatially on two or more of the digitised signals in concert.

Figure 17:
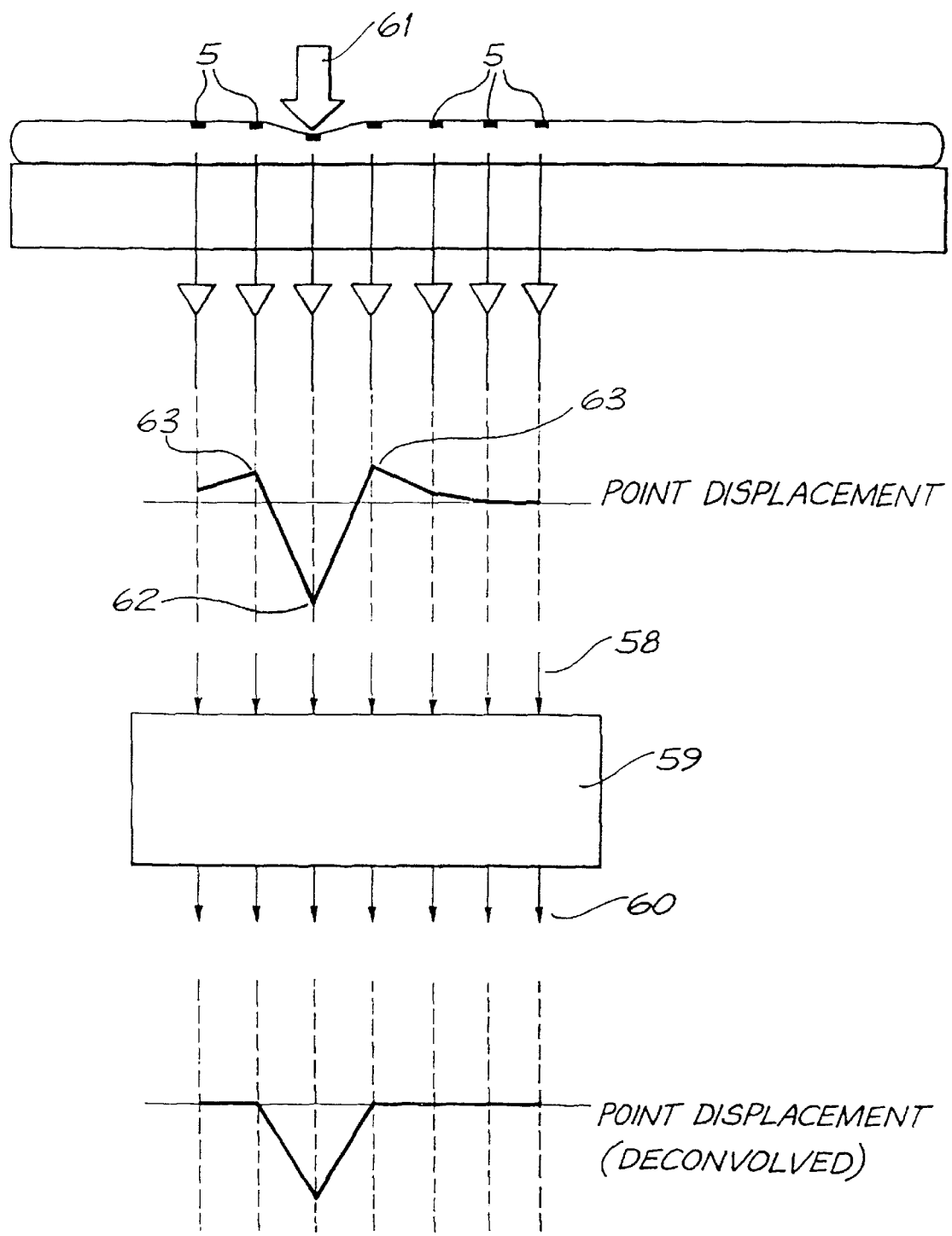
FIG. 17 illustrates the deconvolution of a channel by subtraction of a fraction of the signal on that channel from the two adjacent channels in order to sharpen the spatial response of the channels.

The pre-processing means 59 acts on each channel of digitised signals 58 firstly to equalise the gains of each channel, that is, to remove the variation in amplitude and phase response of each sensor strip 5 relative to the other sensor strips 5, and secondly and optionally to deconvolve the signal of each sensor strip 5 from the effects of adjacent strips 5 (as shown in FIG. 17). Thus processed, the signals are output as pre-processed digitised signals 60.

The above-mentioned deconvolution comprises the subtraction from at least each adjacent channel 63 adjacent to the channel 62 being deconvolved, of a precalculated fraction of the signal measured in said channel 62 such as to remove from said adjacent channels 63 any signal contribution due to physical pressure 61 exerted on the sensor strip 5 corresponding to the channel 62 being deconvolved. The effect of this procedure is to localise or "sharpen" the spatial response for each channel.

Basic Processing

Figure 18A:
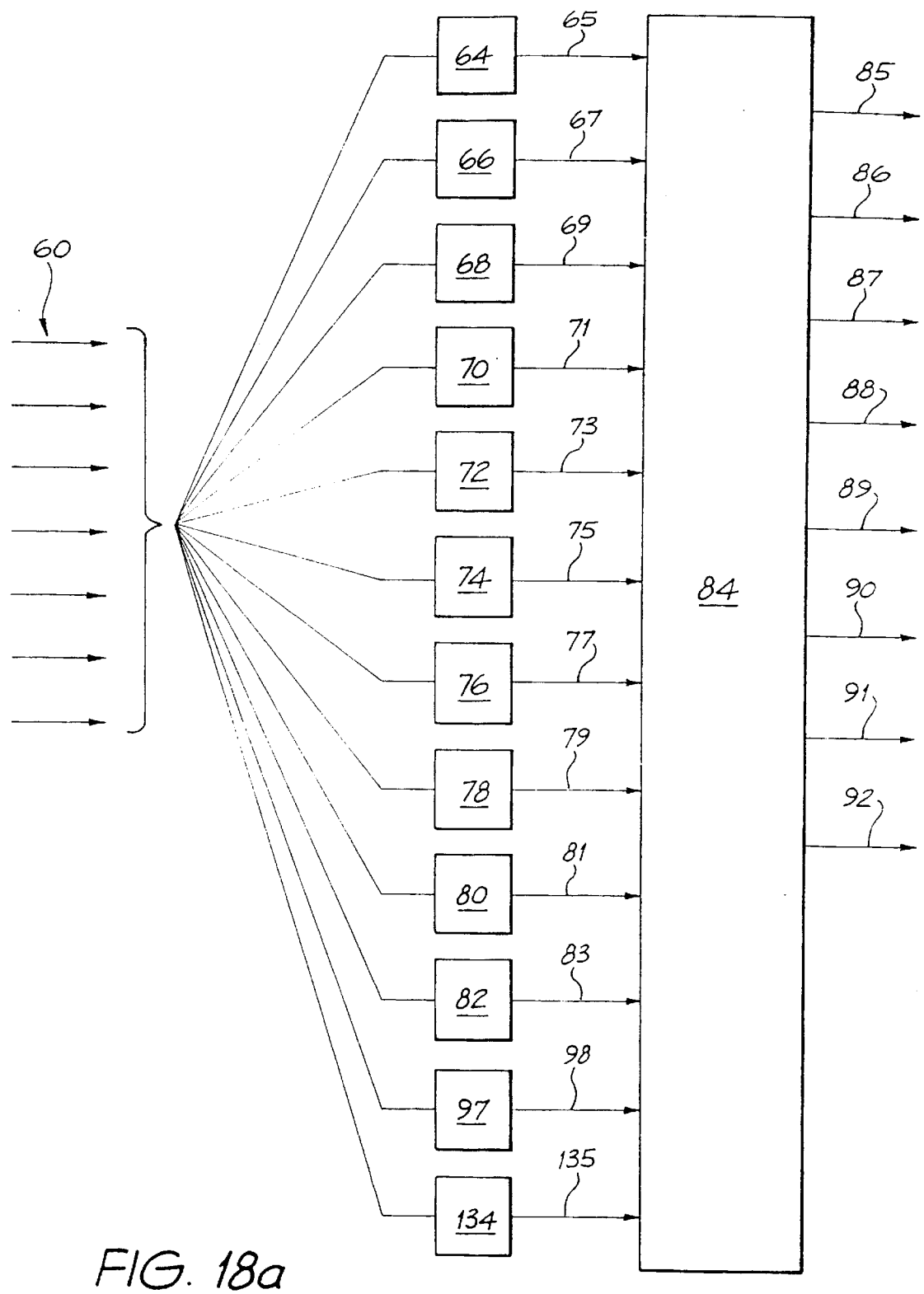
FIG. 18a illustrates the calculation of diagnostic signals from the pre-processed digital signals using basic processing means followed by diagnostic processing means.

Referring to FIG. 18a, the pre-processed digitised signals 60 are then separately input in parallel to a number of basic processing means 64,66,68,70,72,74,76,78,80,82,97 and 134 (again forming part of computing means 104) whose function is to extract particular features from the digitised signals, the features subsequently being used in combination to obtain a diagnosis. Some of said basic processing means act temporally on each individual channel of the said digitised signals while others act spatially in concert on two or more of the said pre-processed digitised signals.

Respiratory Effort

Basic processing means 64 acts on one or more of pre-processed digitised signals 60 to produce a basic derived signal 65 which is a measure of the sum total of the patient's movement, regardless of polarity. The basic derived signal 65 is a measure of the patient's instantaneous respiratory effort ER and is calculated as:

Respiratory effort $$E_R(t) = \sum_{i=1}^{N} \mod s_i(t)$$

where N is the number of sensor strips 5, and $s_i(t)$ is the signal derived from the ith sensor strip 5 as a function of time. $S_i$ therefore corresponds to the displacement of the ith sensor strip 5.

An alternative calculation is:

$$E_R(t) = \sum_{i=1}^{N} s_i^2(t)$$

Basic processing means 66 acts on one or more of pre-processed digitised signals 60 to produce a basic derived signal 67 which is a measure of the integral over a complete breath, or the summed separate integrals over the inspiratory and the expiratory phases, of the sum total of the patient's movement, regardless of polarity. The basic derived signal 67 is a measure of the patient's total respiratory effort $T_R$ for the breath and is calculated as:

Total respiratory effort $$T_R = \int_{breath} \sum_{i=1}^{N} \mod s_i(t) \cdot dt$$

where N is again the number of sensor strips, and mod $s_i(t)$ is the modulus (amplitude) of the signal derived from the ith sensor strip 5 as a function of time.

An alternative calculation is $$T_R = \int_{breath} \sum_{i=1}^{N} s_i^2(t) \cdot dt$$

Respiratory Phase

Basic processing means 68 acts on one or more of pre-processed digitised signals 60 to produce basic derived signal 69 which is a measure of the respiratory phase of the patient. The basic derived signal 69 indicates at what point in the inspiration/expiration cycle the pre-processed digitised signals 60 are being measured and may be calculated in one instance by fitting retrospectively in time a sine wave, as a function of time, to the largest in amplitude of pre-processed digitised signals 60. The basic derived signal 69 associated with specific pre-processed digitised signals 60 is then calculated as the phase angle at whichever point on the aforementioned sine wave coincides temporally with the measurement point reached in said pre-processed digitised signals.

Basic processing means 70 acts on one or more of pre-processed digitised signals 60 to produce basic derived signal 71 which is a measure of the spatial respiratory zero phase point of the patient. The basic derived signal 71 indicates at what position on the movement-sensitive mattress 2 the patient's body changes from exerting positive to negative pressure and changes significantly with the patient's mode of breathing. The signal is calculated as the sensor strip 5 index (n) at which the sums of the positive and negative displacements are equal within a prescribed error, namely:

n is "zero phase point"
when $$\sum_{i=1}^{N-n} s_i(t) \approx 0 - \sum_{i=n}^{N} s_i(t)$$

Corporeal Displacement

Basic processing means 72 acts on one or more of pre-processed digitised signals 60 to produce basic derived signal 73 which is a measure of the average displacement ($P_R$) of the patient. The basic derived signal 73 indicates the degree that the thorax and abdomen of the patient are free to move independently of each other and is thus sensitive to the transition from unobstructed to obstructed, that is, so called paradoxical, breathing efforts.

Such a signal may be calculated as:

$$P_R(t) = \sum_{i=1}^{N} s_i(t)$$

and/or
by observing a change of phase or sign between channels which have been moving in phase for some time (typically some number of minutes)
and/or
a diminution of observed movement in the sensor strips 5 in contact with the abdominal area of the body (rather than the thoracic).

Snore

Basic processing means 74 acts on one or more of pre-processed digitised signals 60 to produce basic derived signal 75 which is a measure of the snore amplitude of the patient. A signal indicative of snore amplitude may be calculated by passing each channel of the aforesaid pre-processed digitised signals through a digital high pass filter with a low frequency cut-off of approximately 10 Hz, then calculating the modulus of each resulting signal, then summing all the moduli and passing the sum through a low pass filter with a high frequency cut-off of between 0.5 and 2 Hz. Basic derived signal 75 is the resultant output of the aforesaid low pass filter.

Basic processing means 76 acts on one or more of pre-processed digitised signals 60 to produce basic derived signal 77 which is a measure of the harmonic purity of the patient's snore, that is, its closeness in form to a simple sine wave. The basic derived signal 77 varies with the type of snore—a non-obstructive snore having a different degree of harmonic purity than an obstructive one. A signal indicative of such above-mentioned snore harmonic purity may be calculated by passing each channel of the aforesaid pre-processed digitised signals 60 through a digital high pass filter with a low frequency cut off of approximately 10 Hz, then selecting the channel with the highest resulting highest amplitude and calculating the instantaneous phase of the signal by, for example, deriving the "analytic" signal from the input signal by passing it through a 90 deg phase shift filter, then differentiating the instantaneous phase, then low pass filtering the resultant differential and differentiating again. Basic derived signal 77 is the resultant output, being inversely proportional to the purity of the snore harmonic content.

Basic processing means 78 yet further acts on one or more of pre-processed digitised signals 60 to produce basic derived signal 79 which is a measure of the harmonic stability of the patient's snore, that is, the accuracy with which one cycle of the snore signal matches its predecessor. The basic derived signal 79 varies with the type of snore—a non-obstructive snore having a different degree of harmonic stability than an obstructive one. A signal indicative of such above-mentioned snore harmonic stability, may be calculated by passing each channel of the aforesaid pre-processed digitised signals 60 through a digital high pass filter with a low frequency cut off of approximately 10 Hz, then selecting channel with the highest resulting highest amplitude and autocorrellating the signal. The number of autocorrellation peaks, normalised for frequency, greater than a preset value, nominally 0.8, present in a rolling window of a preset time, nominally 0.2 seconds, gives basic derived signal 79, being proportional to the stability of the snore harmonic content.

Non-respiratory Movement

The basic processing means 80 acts on one or more of pre-processed digitised signals 60 to produce basic derived signal 81 which is a measure of non-respiratory movements of the patient. The basic derived signal 81 may be calculated by passing each channel of the pre-processed digitised signals 60 through a digital band pass filter with a pass band of approximately 10 to 40 Hz, then calculating the modulus of each resulting signal, then summing all the moduli and passing the sum through a low pass filter with a high frequency cut off of between 2 and 10 Hz. Basic derived signal 79 is the resultant output of the aforesaid low pass filter.

Heartrate

Basic processing means 82 also acts on one or more of pre-processed digitised signals 60 to produce basic derived signal 83 which is a measure of the heartrate of the patient. The basic derived signal 83 may be calculated by passing each channel of the aforesaid pre-processed digitised signals through a digital band pass filter with a pass band of approximately 5–15 Hz, then selecting the channel with the highest resulting highest amplitude and detecting the ballistocardiogram impulse associated with each heartbeat using a matched filter or similar technique. The resultant time interval between matched filter correlation outputs greater than a preset value, nominally 0.8, gives basic derived signal 83. Optionally, to compensate for missed beats, the aforementioned time interval can be divided by two to give a value within the bounds of physiologic possibility.

Alternatively, the abovementioned bandpassed signals may be correlated against past time sets of the same signals in an identical way to that used to determine respiration rate (as described below), to determine basic derived signal 83, the heartrate.

The basic processing means 134 acts on one or more of pre-processed digitised signals 60 to produce basic derived signal 135 which is a measure of the amplitude of the cardioballistogram of the patient. The basic derived signal 135 may be calculated as the unnormalised output of the matched filter correlation technique used to calculate basic derived signal 83, measured at a time coincident with the maximum of basic derived signal 83.

Spatial Effort Point

Basic processing means 97 yet further acts on one or more of pre-processed digitised signals 60 to produce basic derived signal 98 which is the spatial respiratory maximum effort point of the patient. The signal is calculated as the sensor strip 5 index at which the integral over a complete breath of the sum total of the patient's movement, regardless of polarity, is a maximum. First, the integral of the movement of each sensor strip 5 is calculated separately as:

$$R_i = \int_{breath} \text{mod}\, s_i \cdot dt \quad \text{for } i = 1 \text{ to } N$$

where N is the number of sensor strips, and mod $s_i(t)$ is the modulus (amplitude) of the signal derived from the ith sensor strip 5 as a function of time.

An alternative calculation is $$R_i = \int_{breath} \text{mod}\, s_i^2 \cdot dt \quad \text{for } i = 1 \text{ to } N$$

The value of the spatial respiratory maximum effort point is the value of i for which $R_i$ as calculated above is a maximum.

Respiratory Rate

A further basic processing means (not shown) can act on pre-processed digitised signals 60 to produce a further basic derived signal (not shown) which is a measure of the prevailing respiratory rate. This basic derived signal is calculated by correlating the spatial "shape" of the sensor pattern at any given time with the "shapes" of the sensor pattern in past time; the first occurrence of a good correlation (with a coefficient greater than a preset value, typically 0.9) indicates at what time previously a similar pattern occurred, that is, the current respiration rate.

First each channel of the aforesaid preprocessed digitised signals 60 is passed through a low pass digital filter with a high frequency cutoff of approximately 2 Hz and, optionally, the sampling rate of the said filtered signals is decimated down to approximately 20 Hz for subsequent computing convenience. At each sampling point in time, the current spatial set of filtered sensor signals, $$\sum_{i=n}^{N} S_n(t)$$

is cross correlated against the sets sampled at previous times to give a correlation function:

$$C(t - mT) = \sum_{i=n}^{N} S_n(t) \cdot \sum_{i=n}^{N} S_n(t - mT)$$

the maxium value of m for which correlation function C exceeds the aforementioned threshold is the period separating the present from previous, similar phases of breathing, that is, the breath to breath interval. This measurement is performed at each sampling period, generating many estimates of respiration rate per breath. The individual estimates of the maximum value of, m, can optionally be low passed filtered to diminish the effect of transient signal artefacts.

Further basic processing functions can be performed as follows.

'Laboured' Breathing

Many patients with respiratory problems exhibit "laboured" breathing as a symptom of their condition. By "laboured" breathing is meant a physical exertion, associated with inspiration or expiration, that is significantly greater than the normal exertions of breathing. In one patient subgroup, such laboured breathing is caused by an increase in upper airway resistance, particularly on inspiration.

It is known that patients whose upper airways are partially obstructed produce electrical signals in the Static Sensitive Charged Bed that have a higher frequency component—so called "high frequency spiking" (Polo O, "PhD Thesis", republished as a supplement in *Acta Physiologica Scandinavica Vol* 145, *Supplementum* 606, 1992). In the prior art, processing of the aforementioned higher frequency component has been limited to bandpass filtering prior to display as a time varying trace on an oscilloscope or polygraph. In viewing such a display, the trained observer can estimate by eye that a degree of laboured breathing exists but cannot quantify it or diagnose its extent automatically because the magnitude of the signal varies with such parameters as the orientation of the subject with reference to the sensor, his or her size and shape.

One or more of the electrical signals 44 from the movement sensitive bed sensor strips 5 or preprocessed signals 60 are passed through an analog or digital Effort Filter with a passband that rejects both the low frequency signals, predominantly produced by basic respiration, and the high frequency signals produced by snoring and cardiac action. Typically the pass band of the said Effort Filter is from 4 Hz to 10 Hz and after the filter the modulus of the signal is taken and the resulting signal low pass filtered at about 4 Hz to give a signal proportional to the amplitude of the original bandpassed one. The output of the Effort Filter is then subjected to two, parallel processes—firstly the said output is averaged over the entire duration of each respiratory phase, that is, separately over the inspiratory phase and the expiratory phase, and secondly, the maximum amplitude reached by the said output within each respiratory phase is measured and stored. These measurements are termed, respectively, the Average Respiratory Phase Effort and the Maximum Respiratory Phase Effort. The said Effort measurements can be displayed and stored in their own right or, preferably used as inputs to further processing described below.

A significant improvement is offered over existing systems in that there is provided a method of measuring the extent of laboured breathing and determining objectively the degree thereof. Such an embodiment of the invention is amenable to use within automatic respiratory diagnostic systems.

Respiratory Phase Change

Figure 18B:
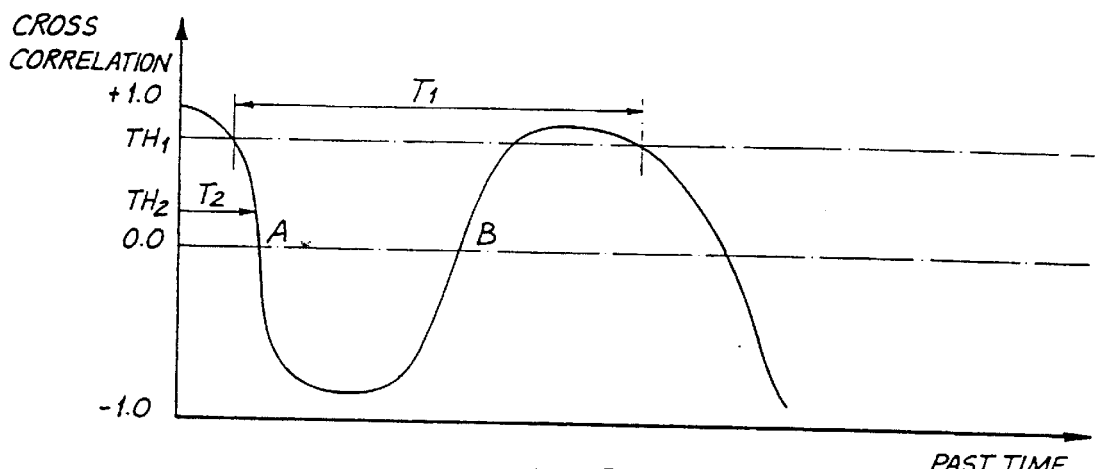
FIG. 18b–f show plots of cross correlation with historical time.

In the automatic assessment of respiratory performance it is advantageous to determine the onset of each of the two respiratory phases, inspiration and expiration. This embodiment consists of the further processing of the cross correlation signal used to determine the respiratory rate. The aforesaid signal is the output of a process that correlates the set of sampled signals from the sensor strips 5 with previous sets of the same signals, stored back in time. For regular breathing, there will be a point in time, one breath back, where the values of the sampled set of sensor signals will be almost identical to the current set. This is evident in the output of the amplitude normalised cross correlation described in the original provisional patent. FIG. 18*b* shows the outputs of the said cross correlation with increasing time into the past. In FIG. 18*b* expiration or inspiration has just started and correlation between the current signal set and its immediate predecessors quickly declines. One breath back, correlation again increases towards +1.0, enabling the current respiration rate to be measured as time, $T_1$, between correlation threshold levels $TH_1$.

Figure 18C:
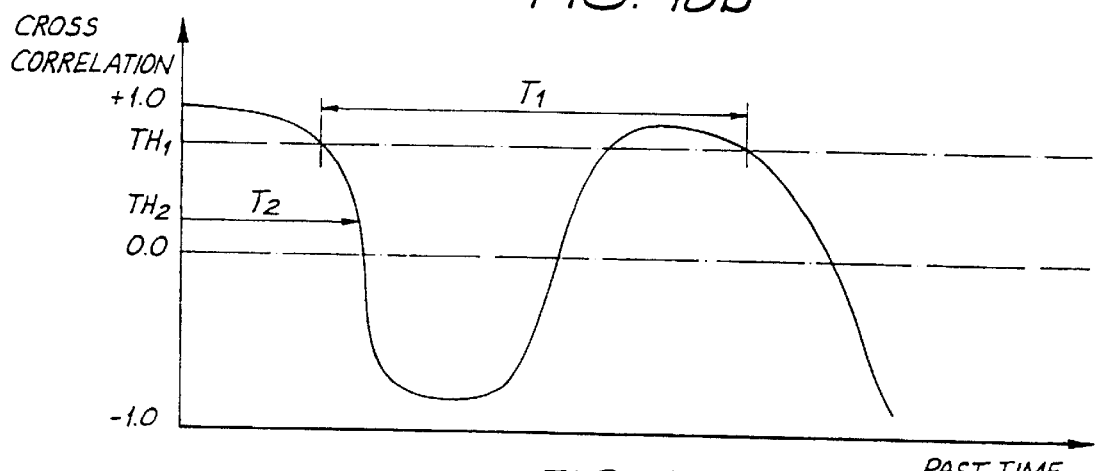
Figure 18D:
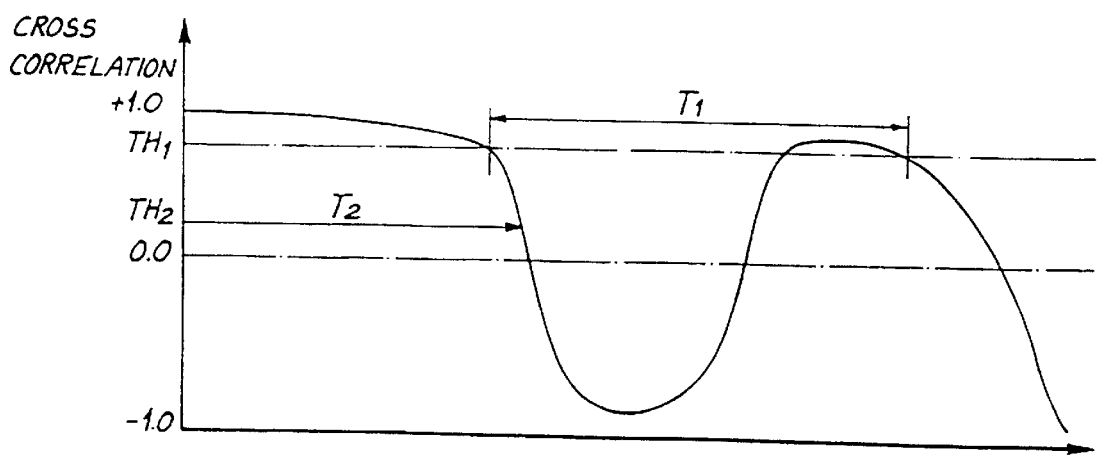

The system monitors the value of the above past time cross correlation signal with time. As time into the inspiration or expiration progresses, the values of each time sampled set of strip signals stabilises, giving an increased span of correlation with the immediate past signals. This is observable in FIGS. 18*b*–*d*, where the time into the past, $T_2$, for the cross correlation signal to fall from a good correlation of almost +1.0 to the negligible correlation threshold, $TH_2$, increases with time. At the end of the respiratory phase, significant past correlation time, $T_2$, is at a maximum (FIG. 18*d*; at the onset of the next respiratory phase, that is the transition between inspiration and expiration or vice versa, the extent of past time correlation and hence the value of $T_2$ drops significantly to the start of phase pattern indicated in FIG. 18*b*. The aforementioned reduction in the significant past correlation time is indicative of a change of respiratory phase. The processing system monitors the value of the said past correlation time and compare it continuously with a threshold value of typically 70% of the maximum reached. When the value of the said time drops below that of the said threshold the end of inspiration or expiration is indicated.

Respiratory Rate I

The system determines the elapsed time between the last two indications of respiratory phase change of method immediately above. This elapsed time is the current breath time, effectively measured at every half breath interval.

Detection of Abnormal Breathing

Figure 18E:
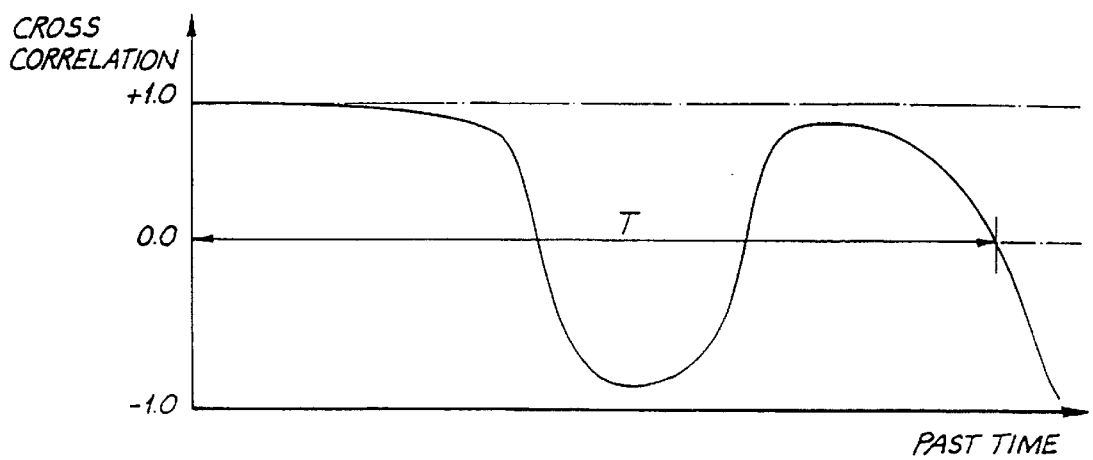

Respiration with a relatively unobstructed airway gives rise to a past time correlation pattern described above and indicated in FIG. 18*e*. A particular characteristic of this correlation pattern is that the correlation values throughout the respiratory cycle tend to be close to either +1.0 (correlation) or −1.0 (anti-correlation), remaining at intermediate values for only a small percentage of the time.

Figure 18F:
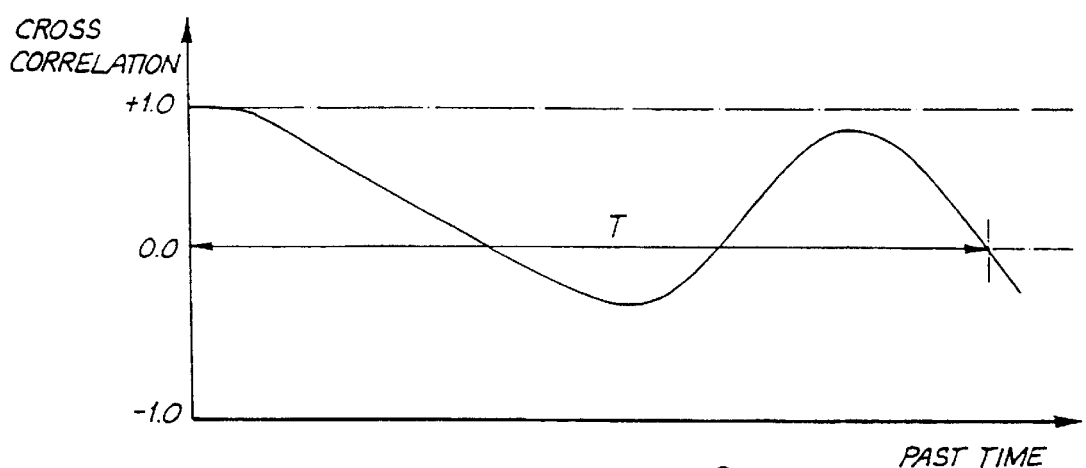

This characteristic is used to distinguish between relatively unrestricted respiration and highly restricted or totally obstructed, so-called paradoxical respiration, in which there can be a significantly more gradual decline in past time away from correlation, and, in which the correlation value no longer approaches the anti-correlation level of −1.0 (FIG. 18*f*). Specifically, the present invention takes the past time correlation values as shown in FIGS. 18*f* and 18*g* and performs two processes in parallel. Firstly, the said values are averaged over the period from the present back in time to the point prior to the last complete breath that the said values fall to a level of insignificant correlation, typically zero; this is indicated by time, T, in FIGS. 18*e* and 18*f*. Secondly, the arithmetic modulus of the said values is subjected to averaging over the same, aforementioned period. Alternatively, the abovementioned averaging period can cover the time between the first fall in past time of the correlation value below the threshold of significance and the similar fall for one breath into the past (not indicated). The abovementioned averages are termed, respectively, the Past Breath Correlation Mean and the Past Breath Correlation Modulus Mean.

The Past Breath Correlation Mean is then compared with a threshold close to zero, typically, 0.25. If the said Mean exceeds the said threshold then the breath is deemed to be abnormal, that is, the inspirational correlation profile does not match in antiphase that of the expiration.

Alternatively or additionally, the Past Breath Modulus Mean is compared with a threshold close to 1.0, typically 0.8. If the said Sum exceeds the said threshold then the breath is deemed to be normal, that is, the correlations during inspiration are antiphase to those during expiration.

Diagnostic Processing

Basic derived signals 65, 67, 69, 71, 73, 75, 77, 79, 81, 83, 98 & 135 plus the abovementioned respiratory rate, laboured breathing, respiratory phase change, alternate respiratory rate and detection of abnormal breathing signals are, in turn, input to diagnostic processing means 84 (forming part of computing means 104) which acts on one or more of the said basic derived signals to produce diagnostic signals 85 through 92.

Occurrence of Obstructive Apnea

Diagnostic signal 85 is indicative of the occurrence of an obstructive apnea.

This may be determined from the following states of the above-mentioned basic derived signals:

1. reduction in basic derived signal 73

$$\left(\text{respiratory displacement } P_R(t) = \sum_{i=1}^{N} s_i(t)\right)$$

compared with 5 minute moving average of basic derived signal 73 (respiratory displacement), plus 2. increase in basic derived signal 65

$$\left(\text{respiratory effort } E_R(t) = \sum_{i=1}^{N} \text{mod} \, s_i(t)\right)$$

compared with 5 minute moving average of basic derived signal 65 (respiratory effort), plus 3. near zero value of basic derived signal 75 (snore amplitude), immediately followed by 4. sudden increase in basic derived signal 81 (non-respiratory movements)

optionally plus 5. the aforesaid state (i.e. coincidence of states 1, 2 and 3 above) may be preceded by an increase in basic derived signal 75 (snore amplitude)

optionally plus 6. a marked reduction in arterial oxygen saturation as indicated by an external oximeter connected to external electrical input 48.

Obstructive Apnea Duration

Diagnostic signal 86 is indicative of the duration in time of the above-mentioned obstructive apnea. This is calculated only if diagnostic signal 85 indicates the occurrence of an obstructive apnea and typically may be determined from the length of time of the coincidence of a reduction in basic derived signal 73 (respiratory displacement) compared with 5 minute moving average of basic derived signal 73 (respiratory displacement), an increase in basic derived signal 65 (respiratory effort) compared with 5 minute moving average of basic derived signal 65 (respiratory effort) and a near zero value of basic derived signal 75 (snore amplitude). Optionally the aforesaid state (i.e. coincidence of states 1, 2 and 3 above) may be accompanied by a marked change in basic derived signal 135 (ballistocardiogram amplitude). Optionally the aforesaid state (i.e. coincidence of states 1, 2 and 3 above) may be accompanied by a marked decrease in basic derived signal 83 (heartrate), followed by a marked increase therein.

Diagnostic Signal Accuracy

Diagnostic signal 87 is indicative of the expected accuracy of the above-mentioned diagnostic signal 85 (obstructive apnea occurrence). This is calculated only if diagnostic signal 85 indicates the occurrence of a said obstructive apnea and typically may be determined from the following states of the above-mentioned basic derived signals:

a marked increase in the ratio of basic derived signal 65 (respiratory effort) with respect to basic derived signal 73 (respiratory displacement), plus a low level during the preceding minute of basic derived signal 81 (non-respiratory movements)

plus, optionally a marked shift of basic derived signal 71 (zero phase point) during the apparent obstructive apnea plus, optionally a marked shift of basic derived signal 98 (spatial respiratory maximum effort point) during the apparent said obstructive apnea.

Occurrence of Central Apnea

Diagnostic signal 88 is indicative of the occurrence of a central apnea. This may be determined from the following states of the above-mentioned basic derived signals:

reduction towards zero in basic derived signal 73 (respiratory displacement) compared with 5 minute moving average of basic derived signal 73 (respiratory displacement), plus reduction towards zero in basic derived signal 65 (respiratory effort) compared with 5 minute moving average of basic derived signal 65 (respiratory effort), plus near zero value of basic derived signal 75 (snore amplitude), followed after a variable period by increase in basic derived signal 73 (respiratory displacement) compared with 1 minute moving average of basic derived signal 73 (respiratory displacement), plus increase in basic derived signal 65 (respiratory effort) compared with 1 minute moving average of basic derived signal 65 (respiratory effort), or, optionally, immediately followed by a sudden increase in basic derived signal 81 (non-respiratory movements).

Central Apnea Duration

Diagnostic signal 89 is indicative of the duration in time of the above-mentioned central apnea. This is calculated only if diagnostic signal 88 indicates the occurrence of a central apnea and may be determined from the length of time of the coincidence of a reduction in basic derived signal 73 (respiratory displacement) compared with 5 minute moving average of basic derived signal 73 (respiratory displacement), a reduction in basic derived signal 65 (respiratory effort) compared with 5 minute moving average of basic derived signal 65 (respiratory effort) and a near zero value of basic derived signal 75 (snore amplitude).

Diagnostic Signal Accuracy

Diagnostic signal 90 is indicative of the expected accuracy of the above-mentioned diagnostic signal 88 (central apnea occurrence). This is calculated only if diagnostic signal 88 indicates the occurrence of a central apnea and may be determined from the following states of the above-mentioned basic derived signals:

no marked increase in the ratio of basic derived signal 65 (respiratory effort) with respect to basic derived signal 73 (respiratory displacement), plus a low level during the preceding minute of basic derived signal 81 (non-respiratory movements)

plus no marked shift of basic derived signal 71 (zero phase point) during the apparent said central apnea.

The above-mentioned diagnostic signals 85 (obstructive apnea indication) and 88 (central apnea indication) may be expressed simultaneously in the case of a mixed apnea, that is, a combination of both types of apnea.

Occurrence of Sudden Body Movement

Diagnostic signal 91 is indicative of the occurrence of a sudden body movement without a preceding apnea. Typically this would be determined from the following states of the above-mentioned basic derived signals and the above-mentioned diagnostic signals:

the absence of diagnostic signal 85 (obstructive apnea occurrence)

plus the absence of diagnostic signal 88 (central apnea occurrence)

plus a sudden increase in basic derived signal 81 (non-respiratory movements).

Degree of Obstructive Breathing

Diagnostic signal 92 is indicative of the degree of obstructive breathing present. Typically this may be calculated from the following states of the above-mentioned basic derived signals:

the ratio of basic derived signal 65 (respiratory effort) to basic derived signal 73 (respiratory displacement) averaged over a 1 minute period or the ratio of basic derived signal 65 (respiratory effort) to basic derived signal 73 (respiratory displacement) averaged over the previous breath plus, optionally the value of basic derived signal 75 (snore amplitude), plus, optionally the inverse value of basic derived signal 77 (snore harmonic purity)

Figure 19:
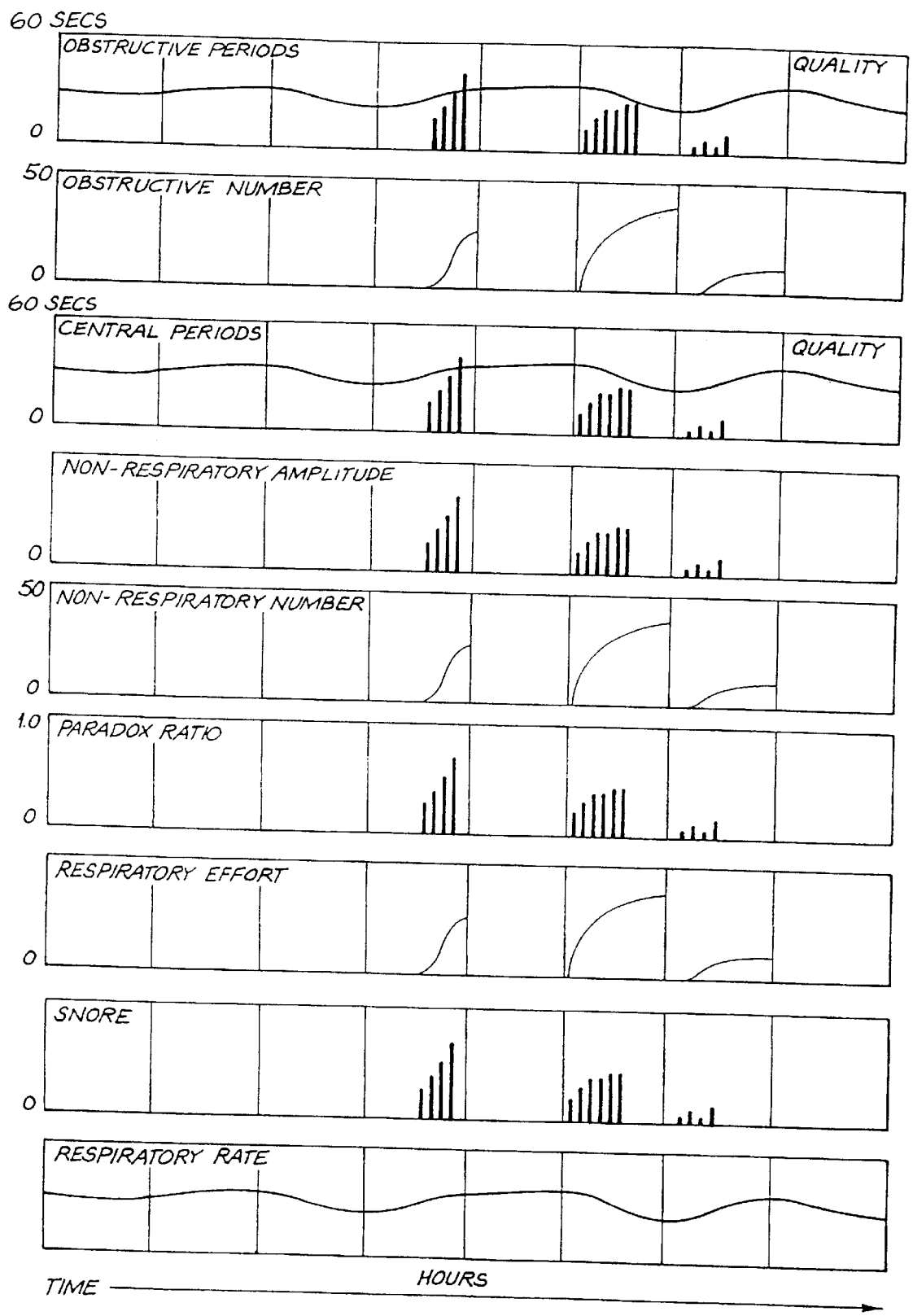
FIG. 19 shows the output of diagnostic signals to display means.

Diagnostic signals 85 through 92 are subsequently:

a) stored to computer disk 107, and/or b) output graphically to display means 106 in one of several forms, for example as a condensed report of the night's study (as shown in FIG. 19), and/or c) output in alphanumeric coded form to physiologic channel output means 110 for subsequent recording and display in association with other electrophysiological signals through a polygraph as described below.

Further diagnostic processing functions can be performed as follows.

Estimation of Degree of Laboured Breathing

An objective measure of laboured breathing can be derived from two of the abovementioned basic processing means. The aforementioned Average Respiratory Phase Effort and Maximum Respiratory Phase Effort signals are processed using the aforementioned indications of respiratory phase change which delineate the temporal boundaries of inspiration and expiration, to derive two signals, respectively the Average Effort Ratio and the Maximum Effort Ratio.

The Average Effort Ratio is determined by dividing the Average Respiratory Phase Effort for the respiratory phase just ended by that determined for the previous phase. Similarly, the Maximum Effort Ratio is determined by dividing the values of Maximum Respiratory Phase Effort for successive phases. For non-laboured breathing, the values of the Average Respiratory Phase Effort and Maximum Respiratory Phase Effort for inspiration and expiration are approximately equal for inspiration and expiration, giving Effort Ratios of approximately unity. If, however, the execution of one phase of respiration, for example inspiration, becomes significantly laboured relative to the other phase, then the Effort Ratios will move away from unity by a factor of two or more. Thus, when deviations of the Effort Ratios for successive respiratory phases drop below typically 0.5 or exceed typically 2 then abnormal effort is indicated and the breath can be defined as "laboured". Two features of the invention are that, firstly, the use of the ratio eliminates the need for scaling the measured signals or knowing details of the subject's orientation and, secondly, knowledge is not required of whether a particular phase is inspiration or expiration. Furthermore, a comparison between the two ratios themselves can give an indication of whether the effort occurs impulsively at the start of the respiratory phase, or in a more diffuse manner throughout the phase: similar values indicate a diffuse effort, a higher Maximum Effort Ratio indicates an initial, impulsive effort.

Estimation of Degree of Snoring

Separately the procedures used to quantify 'laboured' breathing described above may be applied to determine the amount of snoring present, in which case the bandpass frequencies of the effort filters described above are approximately 10 Hz and 100 Hz. The ratios so determined are termed the Average Snore Ratio and the Maximum Snore Ratio.

Classification of respiratory phase—Past Time Correlation Curve Shape

The difference in the speed at which a subject changes from inspiration to expiration is compared with vice versa to indicate which of these changes has occurred. The time taken for the past time correlation value to fall from an Upper Threshold (not shown) to a Lower Threshold (not shown) for the most recent fall of the said correlation (edge 'A' in FIG. 18*b*) is compared to the time taken for the previous transition in correlation between the same thresholds (Curve 'B' in FIG. 18*b*). if the latter transition is slower then the current phase is inspiration, if faster, expiration.

Classification of respiratory phase—Use of Effort Ratios

Particular subgroups of respiratory ailments are characterised by the occurrence of laboured breathing in a particular phase of respiration. Thus, for example, sufferers from Obstructive Sleep Apnea and most other upper respiratory tract disfunctions will work harder on inspiration than expiration. The system compares the Average Effort Ratio and/or the Maximum Effort Ratios with threshold values typically of 1.2 and 0.8. If the Ratios exceed the upper threshold then the last phase was an inspiration, if it is less than the lower threshold, then an expiration. Alternatively or additionally, the abovementioned Average Snore Ratio and Maximum Snore Ratios may also be used to classify the respiratory phase.

Classification of respiratory phase—Use of Mean Strip Value

The system makes use of the fact that in most patient groups inspiration and attempted inspiration is associated with expansion of the thorax, by processing the signals from a selected range of sensor strips from the top location (normally adjacent to the patient's neck or scapulae) down to the approximate level of the patient's waist. The signals from the said range of strips is summed and that sum compared with zero. The transition of the said sum from a negative value to a positive one (associated with the stretching of the said sensors) is an indication of inspiration while the reverse transition, from positive to negative, is indicative of expiration.

Classification of respiratory phase—Voting

Particular groups of patients with peculiar or mixed pathology can produce conflicting indications of inspiration when subjected to the several abovementioned methods of determining respiratory phase. This embodiment takes as input the output from a selection of the abovementioned methods and derives a weighted vote as to which phase is present. If the said vote is above the Inspiratory Vote Threshold then an inspiration is indicated, if below the Expiratory Vote Threshold, then an expiration. If the said vote lays within the two thresholds then an Uncertain Phase is indicated.

Control of CPAP Treatment Apparatus

Figure 20:
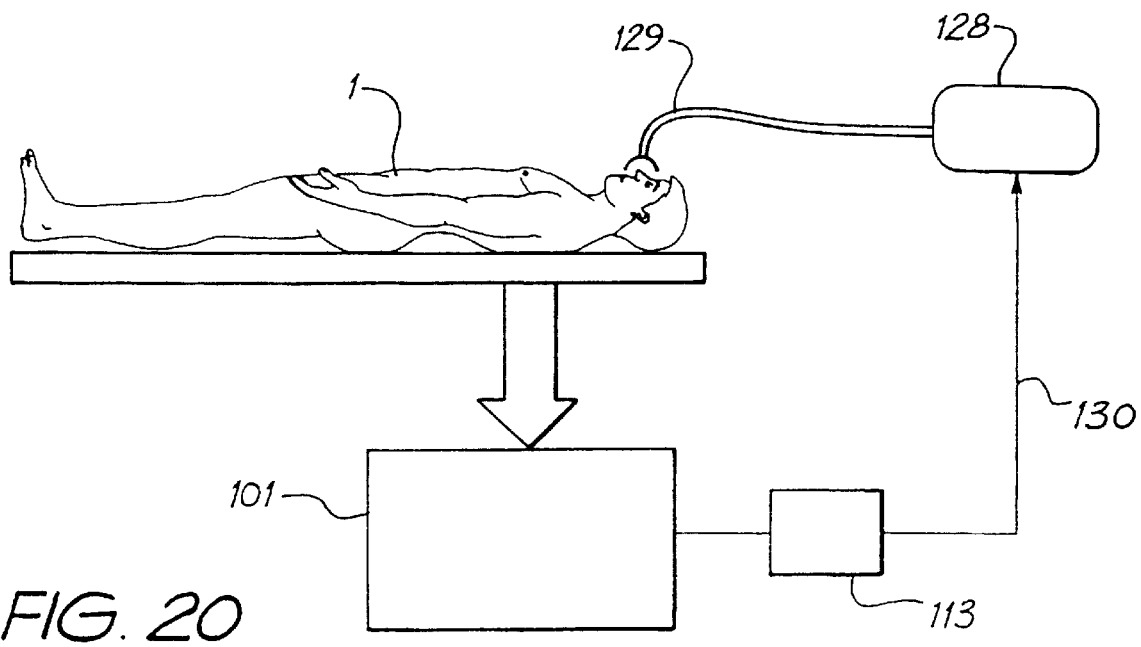
FIG. 20 shows the control of a Continuous Positive Airway Pressure (CPAP) flow generator by the new system.

Referring to FIG. 20, the diagnostic signals 85 through 92, and signals representative of the degree of laboured breathing, the degree of snoring and the classification of respiratory phase, can be used as part of a closed loop to determine and/or control the pressure setting of a Continuous Positive Airway Pressure (CPAP) treatment machine comprising a flow generator 128 that treats obstructive sleep apnea via air delivery tube and mask assembly 129. A monitoring system 101 measures the respiratory parameters of the patient 1 in the manner described above and, if obstructive respiratory events are observed, transmits a control signal 130 to the CPAP flow generator 128 via CPAP control means 113. The control signal 130 increases the treatment pressure if obstructive events are observed and slowly decreases it in the absence of obstructive events.

The aforesaid process of pressure control may be used either as a means of continuously controlling the treatment pressure during the time the patient sleeps or to determine, over the course of one or more nights, the optimum static treatment pressure to which the CPAP flow generator 128 should be set for continuing, subsequent treatment in the absence of the monitoring system 101.

Thus, additionally and separately the aforesaid process of pressure control may be used to determine the pressure to which a CPAP treatment machine must be set for subsequent nights' treatment by the CPAP flow generator 128 alone. In this usage, monitoring system 101 is attached to the CPAP flow generator 128 for a diagnostic period comprising a small number of initial nights, typically between one and five, wherein it controls the pressure of the said CPAP flow generator 128 to limit the number of respiratory obstructive events experienced by the patient. At the end of each night the CPAP flow generator 128 is left programmed with the pressure determined by monitoring system 101 as the optimum for the limitation of the respiratory obstructions. At the end of the diagnostic period the monitoring system 101 is disconnected from the CPAP machine leaving the said machine programmed to the optimum treatment pressure determined.

In the above-mentioned diagnostic period monitoring system 101 follows a set protocol for determining the pressure setting or settings for the CPAP treatment machine. This protocol is open to modification by clinical staff but typically determines the range of pressures needed to reduce the number of apneas and hypopneas to below a preset number, typically 6 per hour. The protocol makes use of above-mentioned diagnostic accuracy indicators 87 and 90 plus other means to reduce the effect of artefacts causing too high a pressure determination. The protocol may advantageously take into consideration diagnostic measurements made over several nights. The above-mentioned diagnostic period can be repeated, for example annually, to maintain the setting of the CPAP flow generator 128 near its optimum.

In the above-mentioned diagnostic period monitoring system 101 produces a report at the end of said diagnostic phase that indicates the main physiological observations of the study and which may assist in the choice of CPAP treatment machine type. Additionally, the report highlights the occurrence of anomalous respiratory behaviour, including the occurrence of central apneas, that may contraindicate conventional CPAP treatment.

It is sometimes advantageous in sleep studies to have a moving or still image of the patient at various times during the night, particularly in coincidence with notable respiratory events. Conventionally, time synchronised video cassette recorders (VCRs) are used, allowing retrospective access to relevant sections of the video tape via computer control. One problem with this arrangement is the need for a video player to effect playback. The invention uses the monitoring system 101 to trigger a video camera that is aimed at the patient so that only the frames immediately preceding and succeeding a notable respiratory event are recorded as a video clip.

Further, using existing MPEG type compression techniques, the aforesaid video clip may be digitised and stored on computer disk 107 with the rest of the physiological information. This allows, on subsequent review, the replay of the video clip in a window on the computer screen at the same time as the physiological data is being observed, without the need for a video player.

As an alternative implementation, particularly for home use, the main recording medium 107 may be the tape of a conventional VCR, the video channel of which records the patient video clips, the audio channel of which records, in digitally modulated form, such as the output of a line modem, a combination of the above-mentioned digitised signals 60, the above-mentioned basic derived signals 64 et seq. and the above-mentioned diagnostic signals 85 et seq.

The recording of snore is also a factor in the monitoring of partially obstructed breathing and there remain subtleties of sound that need the human ear to determine. Thus in review mode the option exists for listening to the snore component of the originally recorded signals, processed for snore detection using the high pass filter as in the derivation of basic derived signal 75 can optionally be played out in real time via sound output means 114, typically a multimedia sound card such as those sold under the registered trademark "SOUNDBLASTER", connected to computing means 104. Another option allows the snore signals to be listened to at a review speed faster than real time.

Figure 21:
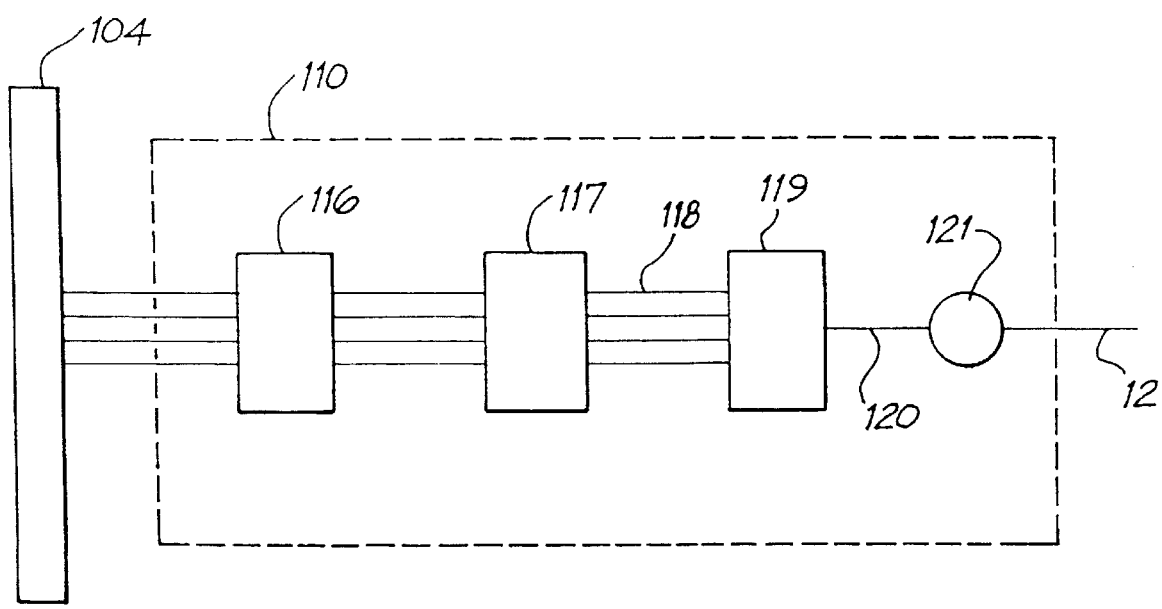
FIG. 21 shows a polygraph input means connected to the computing means, for allowing diagnostic information to be displayed on a polygraph using a spare analogue input channel of the polygraph.

Referring to FIG. 21, polygraph input means 110 is provided as a means of integrating the system described above with existing clinical recording systems in both sleep laboratories and other clinical environments such as intensive therapy and coronary care units. The polygraph input means 110 provides a method of outputting from the system indications of the states of diagnostic signals 85–92 in a form that can be input to the recording system of, for example, a polygraph (shown in FIG. 23) via a physiological input channel of the polygraph. The advantage of the polygraph input means 110 is that no specialist interface need be available in the polygraph, only an unused analogue physiological input channel such as that used for an ECG or EMG, with an input range of between approximately 10 mV and 1 V. Once the signal is input to the polygraph it can be automatically reviewed in conjunction with the conventional input signals using the standard review procedure of the polygraph.

As shown in FIG. 21, polygraph input means 110 comprises computer interface means 116 which is connected to an at least 4 bit wide parallel digital output port of computing means 104, isolation means 117 which electrically isolates the parallel digital outputs of computing means 104 from the isolated digital outputs 118. The isolated digital outputs 118 are connected to an isolated digital to analog converter (DAC) 119, the output 120 of which is attenuated by attenuator 121 and presented as an input 122 to a physiological signal input channel of a polygraph.

The polygraph input means 110 thus allows the input to a polygraph of a series of analog voltage steps, the amplitude of the steps being determined by the digital input applied to the isolated DAC 119.

Figure 22A:
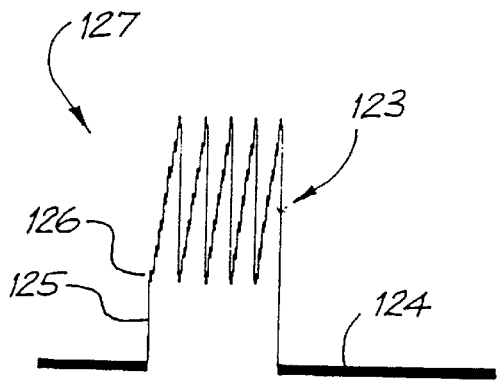
FIGS. 22a and 22b show graphs of voltage against time, and the tracing of symbols on the polygraph display.

By rapidly changing the levels of the steps in a predetermined pattern, the output voltage of the polygraph input means 110 may be caused to trace letters and numbers that are recorded by the polygraph as a conventional analog input signal. FIG. 22a shows a graph of voltage against time of the 7 by 5 element matrix 123 that is used to construct one of the alphanumeric characters 127. Baseline 124 is the voltage output when the system is idling. Fast transitions 125 between dots 126 on the aforesaid matrix are almost invisible on the review screen, leaving the dots, for which the voltage is held constant for a preset time, visible as the matrix.

Figure 22B:
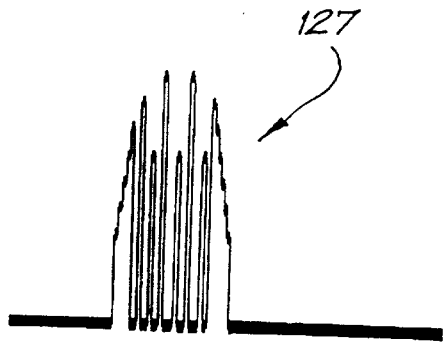

If the display of a particular character does not require a dot in a particular matrix position the said output voltage is returned to the baseline 124 for the duration of the said dot. In this manner a character may be traced out. FIG. 22b indicates the tracing necessary to display the letter "A".

Figure 23:
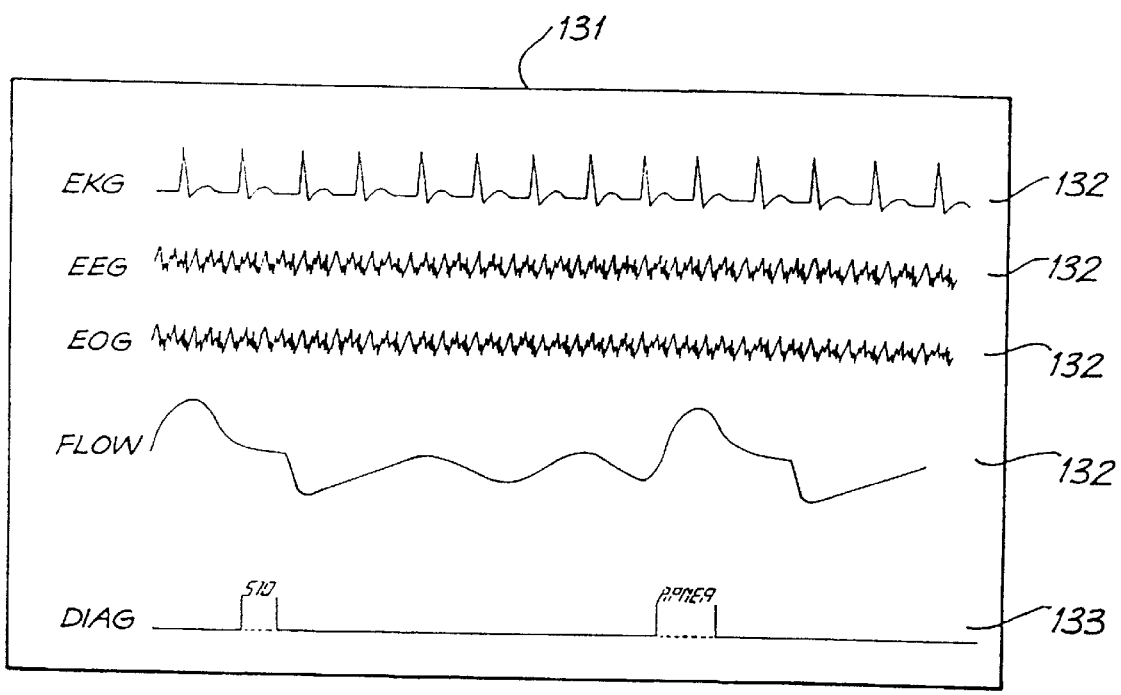
FIG. 23 shows the output of alphanumeric forms of diagnostic variables to the polygraph display.

The aforesaid facility enables computing means 104 to output alphanumeric forms of a selection of diagnostic variables 85–92 to the polygraph, shown in FIG. 23, allowing simultaneous comparison on the polygraph display 131 of the conventional physiological signals 132 being recorded and the diagnoses 133 of the system described above.

By using system 101 with a patient who is undergoing treatment with a CPAP flow generator, the effectiveness of the treatment may be assessed by determining the residual number of obstructive apneas that occur using the above-mentioned techniques.

The aforesaid assessment of effectiveness may also be used to verify that the patient has, in fact, been submitting to treatment by the CPAP flow generator or has been avoiding the same. System 101 can, therefore, also be used as a compliance monitor for CPAP treatment.

Further embodiments will now be described with reference to FIGS. 24 to 33.

Figure 24:
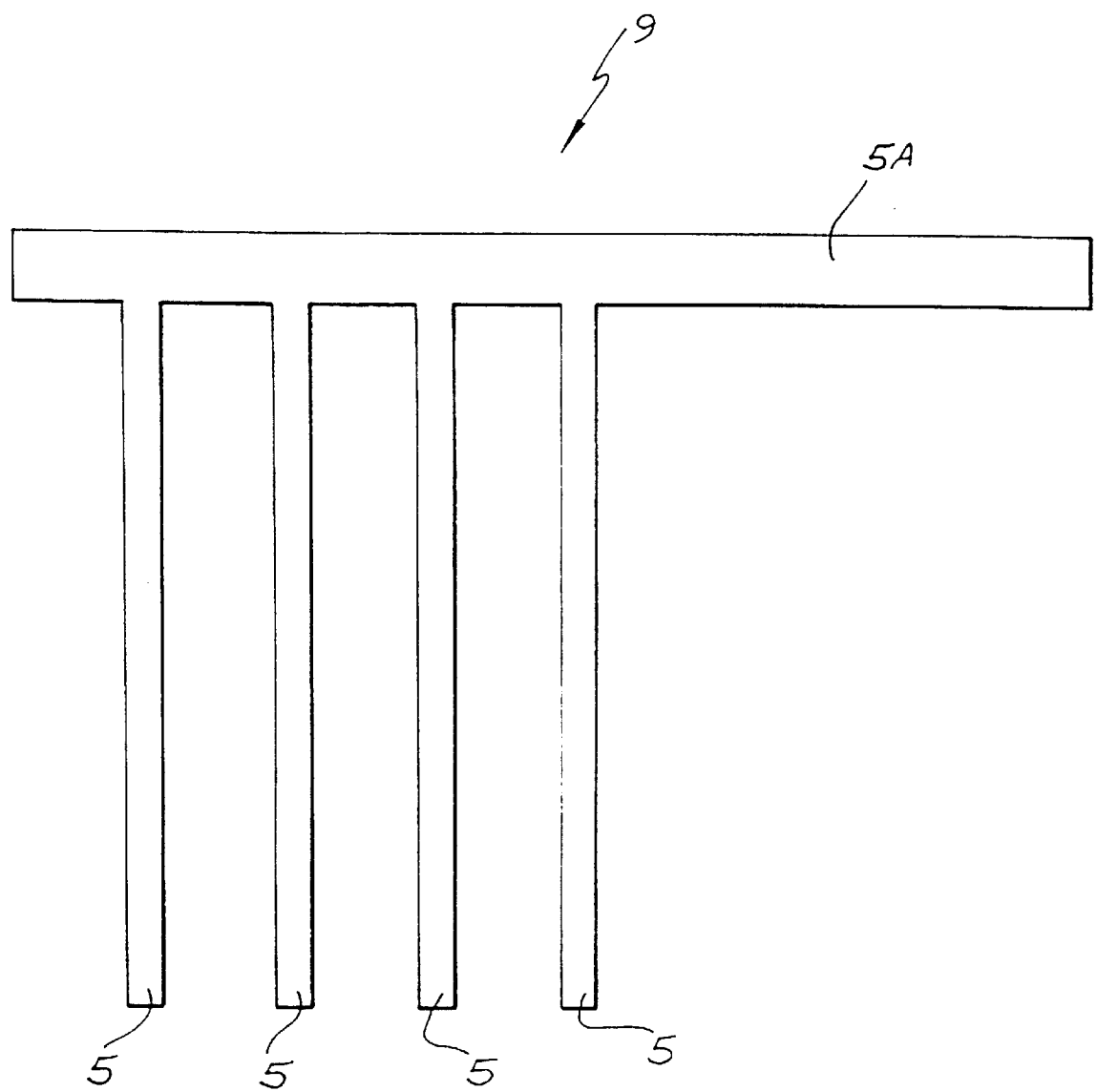
FIG. 24 shows an alternative means of providing a plurality of sensor strips, in which the sensor strips are integrally formed from a single PVDF sheet.

A die cut part 5 is seen in FIG. 24 where a number of sensor strips 5 are cut out from a single sheet of PVDF from which is also formed tail strip 5A. Separate conductive tracks 17 and 17' on each face of each of the sensor strips 35 (FIG. 25) are formed by selective etching or printing at the metallisation layers of the tail strip, 5A to conduct the sensor signals to bus connector 42A.

The PVDF film material is normally only produceable in strips that can be many metres long but which have a restricted width that may be too narrow to allow the manufacture of a large one-part multistrip assembly 9 in the form visualised in FIG. 24. The one-piece form thus displayed is advantageous from a manufacturing point of view— whereby all the strips 5 are part of a single, die cut sheet and, further, in which the electrical connections from each strip 5 may be conducted from the strip via metallisation on integral tailstrip 5A.

Figure 25:
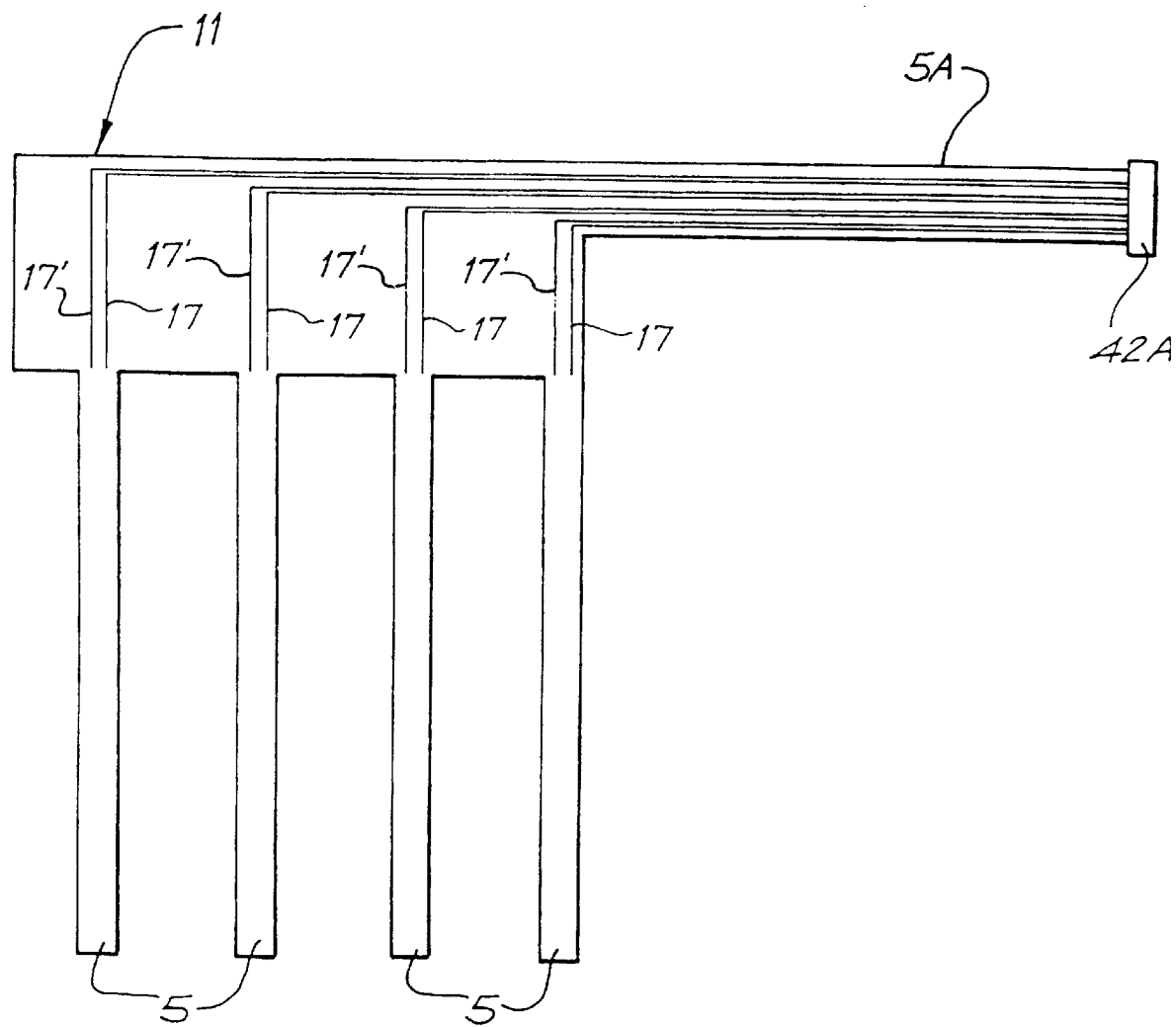
FIG. 25 shows conductive tracks on the embodiment of FIG. 24.

Advantages bestowed by the embodiment of FIGS. 24 and 25 are:

(a) cheaper cost of manufacture
(b) more closely matching of sensor electrical characteristics
(c) more precise location of sensor strips within the movement sensitive mattress
(d) additionally, the provision of an integral strengthening and location element which stabilises and orients the sensor strips.

Figure 26A:
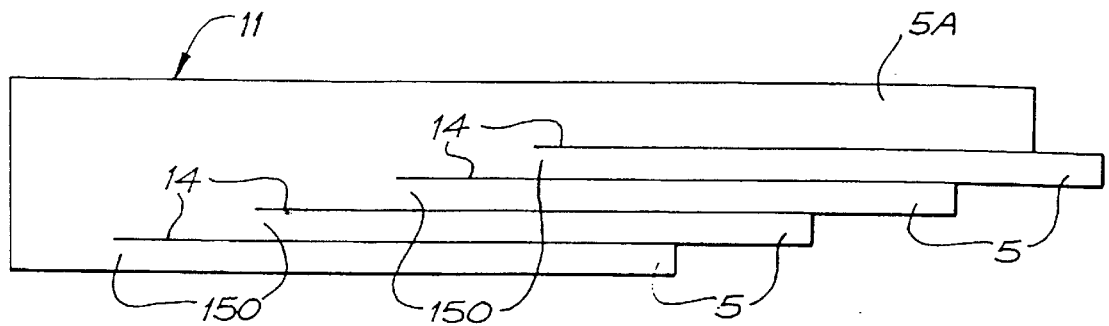
FIG. 26a shows an alternative to the embodiment of FIGS. 24 and 25, in which the sensor strips, are cut from a narrower PVDF sheet and then folded through 90° as shown in the next figure.
Figure 26B:
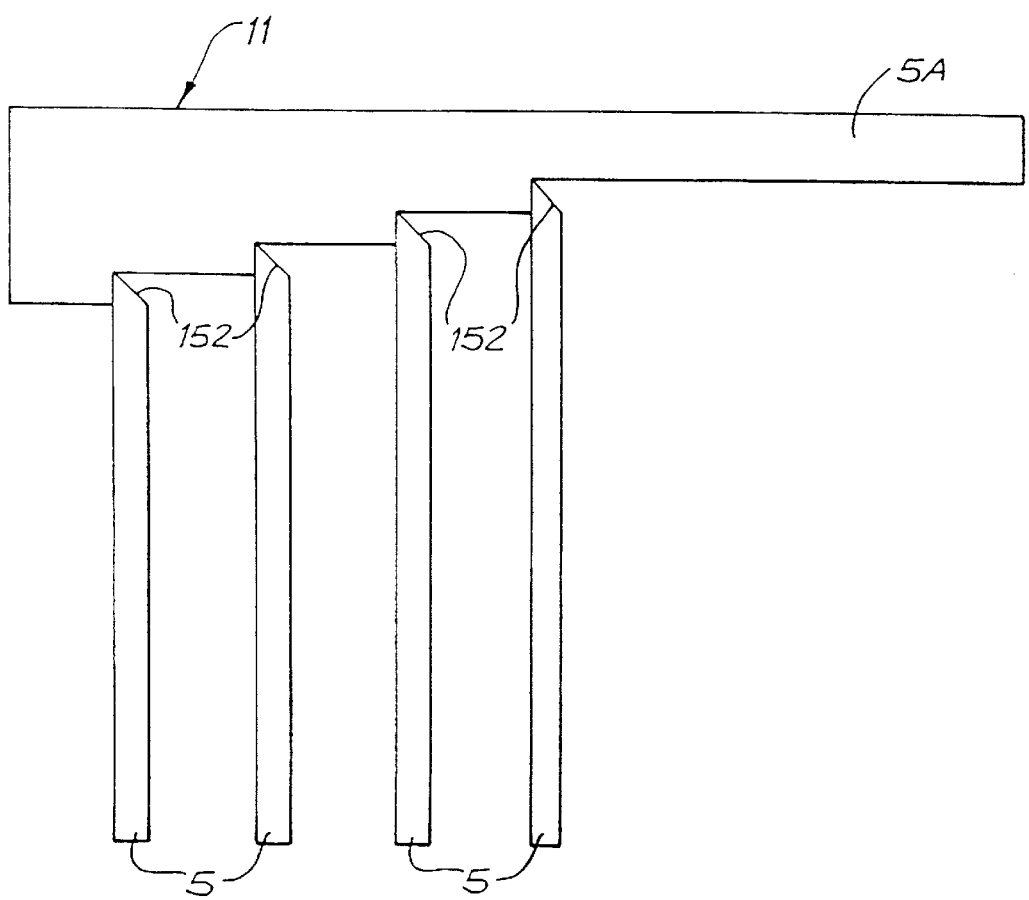
FIG. 26b shows the folding of the sensor strips through 90° while remaining integrally connected to a tail strip.

FIG. 26 shows a further embodiment, which involves the cutting of a relatively narrow (typically 6 cm wide) sheet of PVDF 11 with a pattern illustrated in FIG. 26a, consisting of a number (typically between 4 and 15) of staggered parallel cuts 14 separated by the required width of each sensor strip (typically 1 cm), and of length equal to that required in the aforesaid sensor strips 5, typically 60 cm. The parallel cuts dissect out from the PVDF film, strips 5 whose length is limited only by the length of the said film and not its breadth. Subsequent to the aforesaid dissection, each of the strips 5 is folded into a position 90 degrees from its original orientation at its base 150 via a crease 152 oriented at 45 degrees to the said cuts (FIG. 26b). The residual unfolded element of PVDF sheet 10 serves as an integral tail strip 5A which conducts the electrical signals away from the said sensor strips to a remote electrical connector. Thus can be achieved the goal of producing a single piece sensor system from a film of restricted width.

Figure 27A:
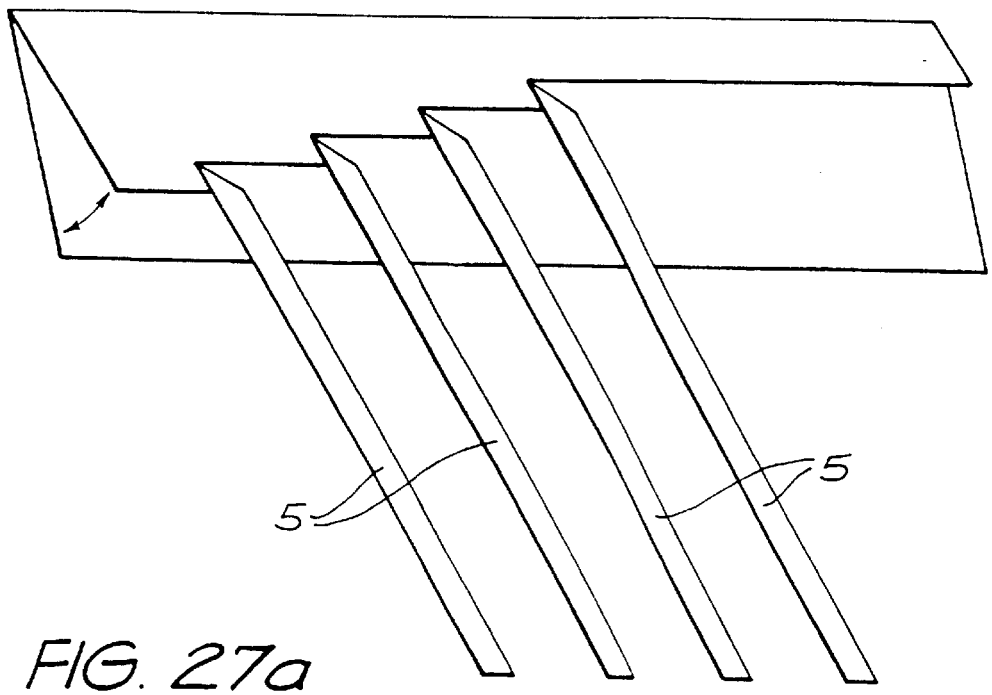
FIGS. 27a and 27b show an embodiment which is the same as that of FIG. 26, except that a broader tail strip is used, so that the tail strip can be folded beneath the sensor strips to provide greater support.
Figure 27B:
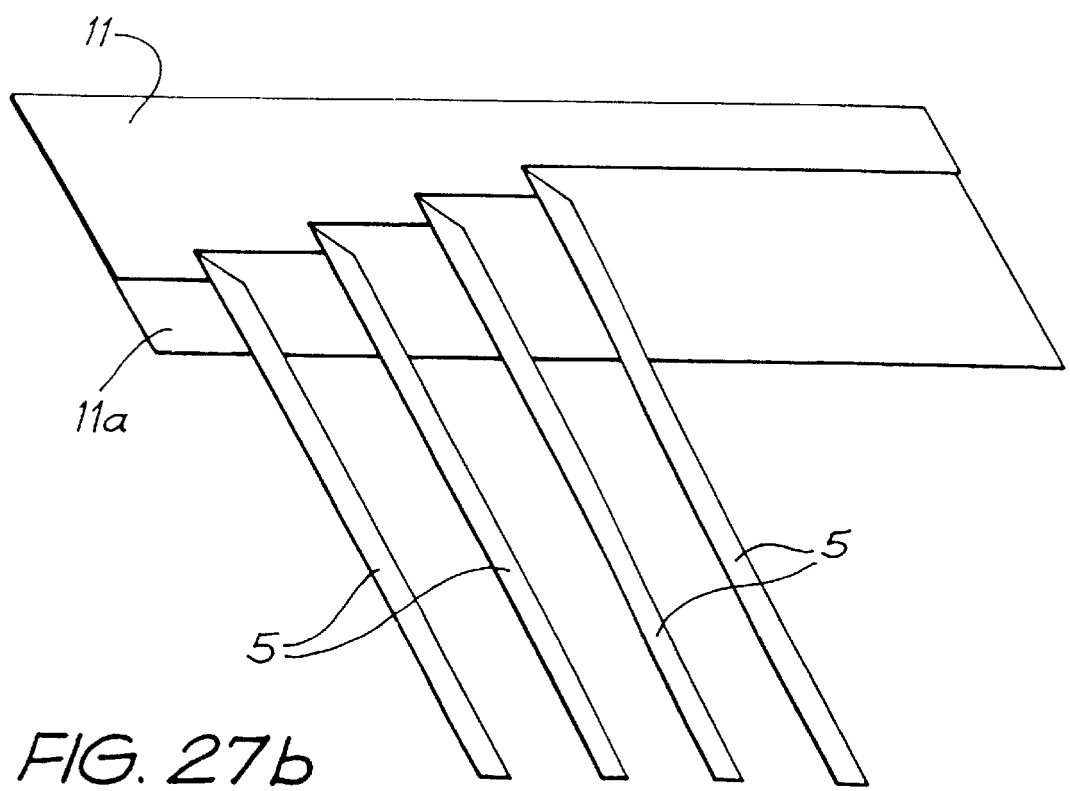

Additionally, PVDF sheet 11 may be manufactured with stabilising element 11a (FIG. 27a) consisting of an integral portion of the said sheet which folds underneath and is glued to the sheet and to the folded sensor strips 5 (FIG. 27b). The said 45 degree creasing of the strips 5 is thus immobilised, thereby removing any tendency for the strips 5 to return elastically to their original orientation.

Figure 28:
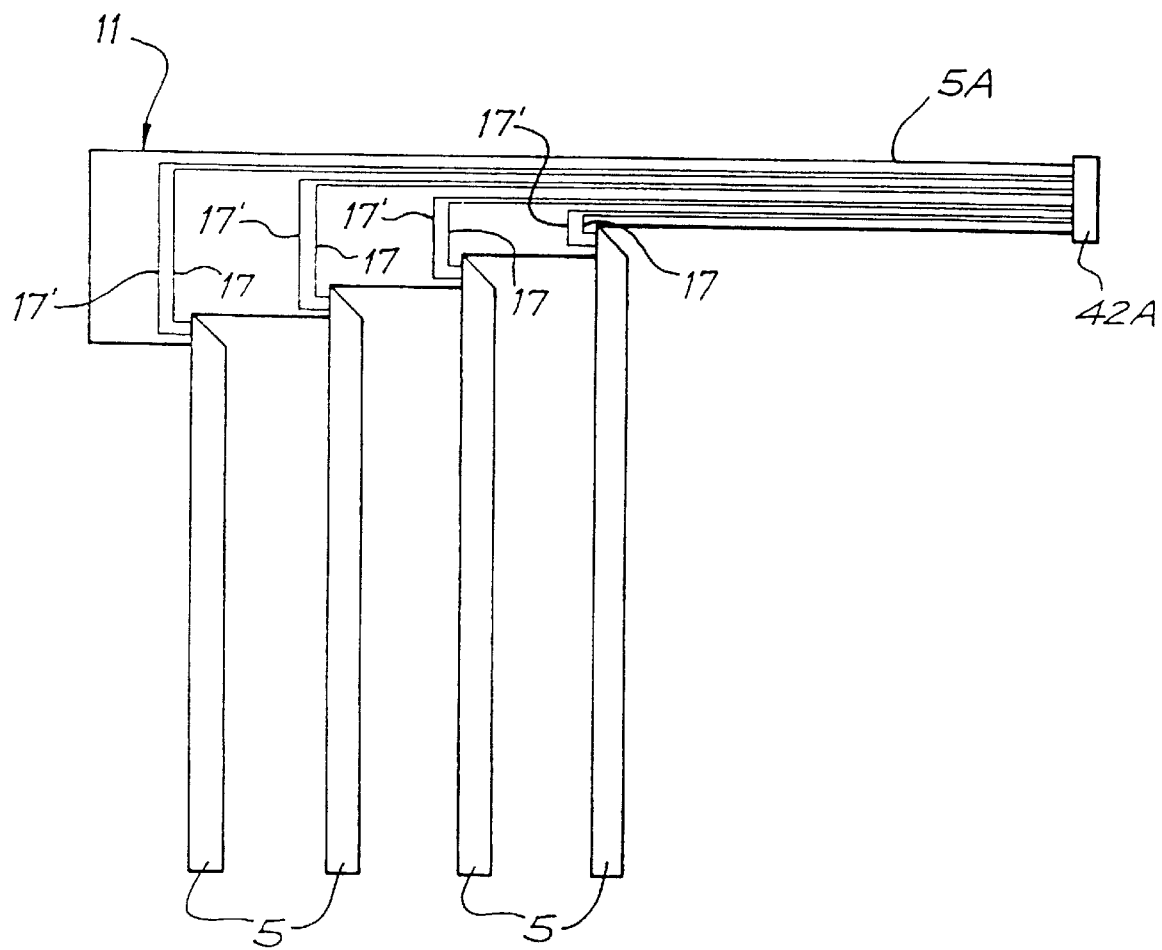
FIGS. 28 and 29 show conductive strips on the embodiment of FIG. 26.

FIG. 28 shows in more detail the electrical connections 17 from each sensor strip 5 along tail strip 5A to bus connector 42A. Normally there will be two separate connections 17 and 17' from each of the sensor strips 5, one from each face.

Figure 29A:
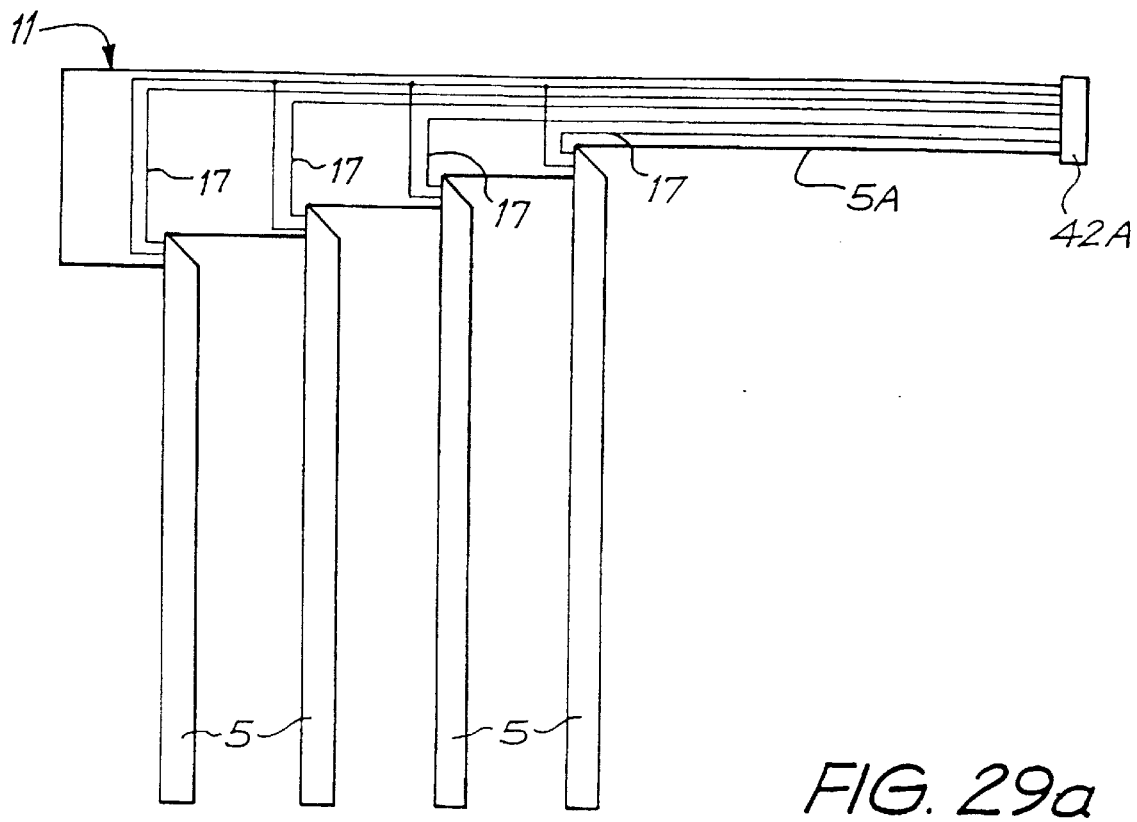

In another, simpler configuration, one face of each of the strips 5 is connected in common and that single common connection is conducted to bus connector 42A along with the single connections from the obverse sides of each individual strip (FIG. 29a).

Figure 29B:
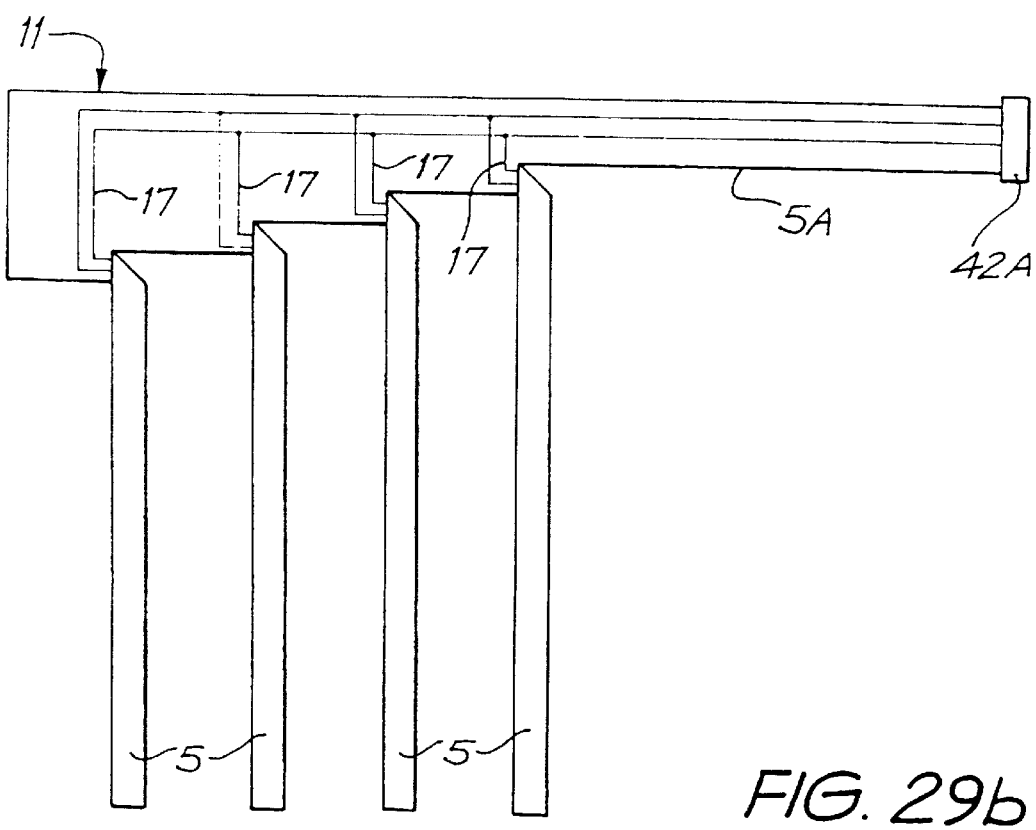

In a further simplification, all or some of the top faces of the said sensor strips may be connected in common and, separately, all the obverse faces may be likewise connected in common, to give just two electrical connections to the assembly (FIG. 29b). Such a simplification no longer allows the signal from each of the said sensor strips to be recorded separately, rather the output electrical signal is the sum of all the individual responses.

Optionally, further conductive layers or films may be applied over the entire area of the PVDF film 11 to shield the aforesaid connections from external electrical interference.

Figure 30A:
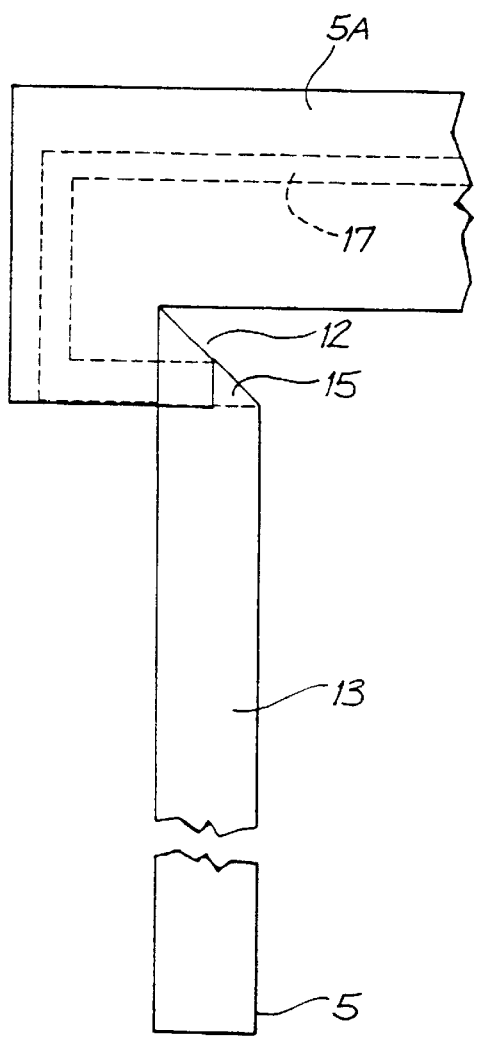
FIG. 30 shows the metallisation on each side of one of the sensor strips.
Figure 30B:
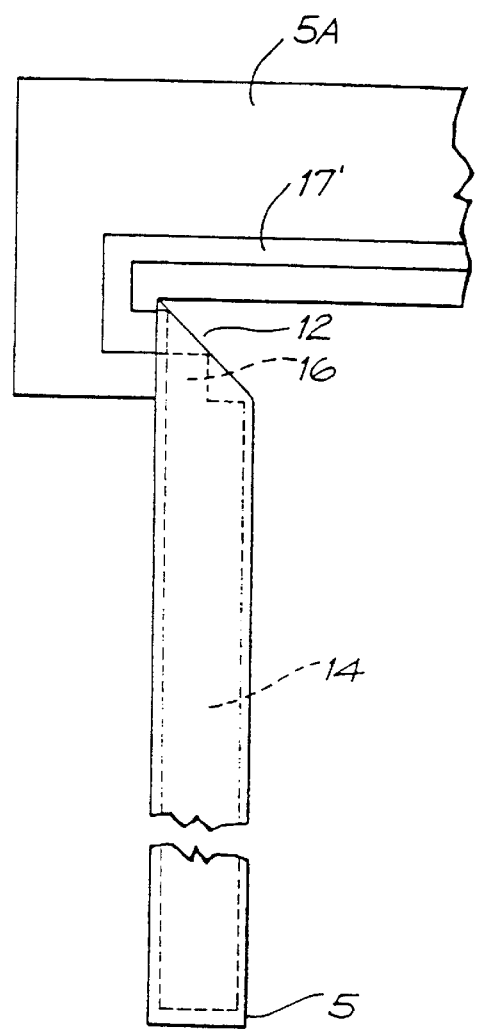
Figure 31:
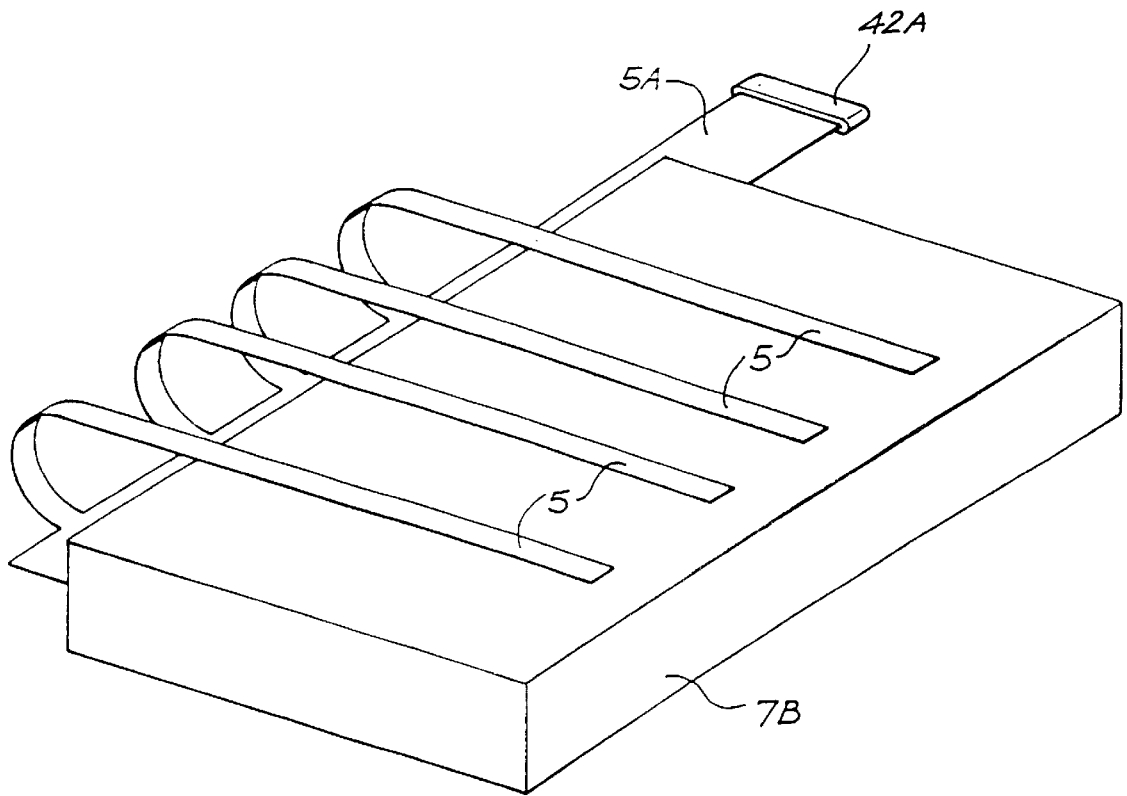
FIG. 31 shows the sensor strips wrapped around one edge of a foam sheet

FIGS. 30a and 30b show in more detail the design of the conductive metallisation 13 on the top surface (FIG. 30a) and conductive metallisation 14 on the obverse (FIG. 30b) which collect the strain-generated charge from the strip and conduct it to the bus connector 42A. Electrical charge is only conducted from the faces of the sensor strips 5 when each opposing face is metallised with conductive layers which overlap. In order to limit the area of sensitivity to that of the strip itself, the opposing metallisation patterns are staggered in the region 15 & 16 of said 45 degree crease and, thereafter, on tail strip 5A. This renders the region of the said crease and the tail strip insensitive to any strains that maybe imposed thereon. This is important because the creasing causes disproportionate strain to be experienced at the crease.

In all the above-mentioned sensor configurations the separate option exists (FIG. 31) to curl sensor strip 5 round the edge of mounting foam sheet 7B, allowing the tail strip 5A and bus connector 42A to be located away from patient contact. This advantageously removes any difference in stiffness that may be felt by the patient when lying on tail strip 5A or bus connector 42A and further protects the said bus connector and associated wires from potential physical damage.

When placing a said movement sensitive mattress on top of a conventional mattress, if the lateral dimensions of the two mattresses differ then the patient on the bed may well be discomfited. By making full use of the inherent thinness of the above-mentioned sensor assemblies the complete movement sensitive mattress may be mounted in an assembly less than 3 mm in thickness, allowing its easy and comfortable location on a range of conventional mattress sizes.

The thin movement sensitive mattresses described above can be regarded as a movement-sensitive sheet.

Figure 32A:
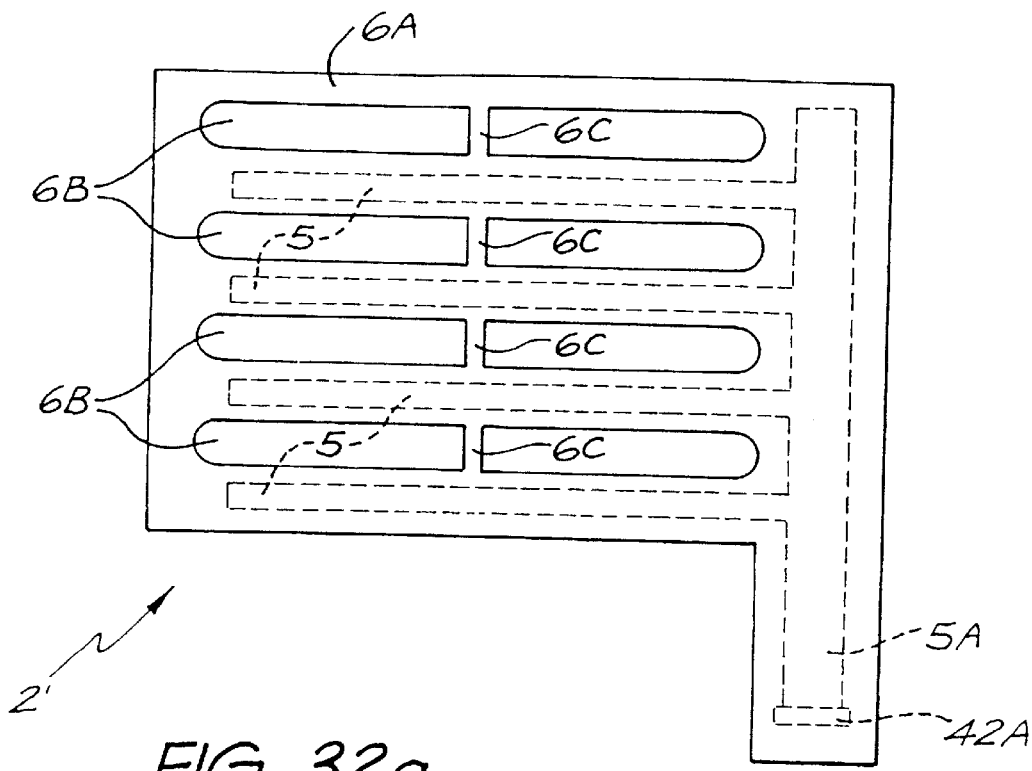
FIGS. 32a, 32b and 32c show movement-sensitive sheets comprising the embodiments of any of FIGS. 24 to 30.

It may be desirable that the sensor strips 5 be enclosed in a waterproof envelope. However, the use of a sheet of neoprene or similar rubber to effect the waterproofing function can be clammy and uncomfortable. In order to improve comfort in this regard the construction of FIG. 32a is used. Movement-sensitive mattress or sheet 2' is constructed as described above with sensor strips 5 connected to tail strip 5A and bus connector 42A, the assembly thereof being sandwiched between thin neoprene or other suitably waterproof, flexible sheet 6A. The said sheet 6A is, however, perforated with holes 6B that allow the assembly to "breathe"—that is, to facilitate the diffusion of humidity from the area in contact with the patient to the conventional bedding beneath the said movement sensitive mattress or sheet. The location of the sensor strips 5 are optionally located by web components 6C.

Figure 32B:
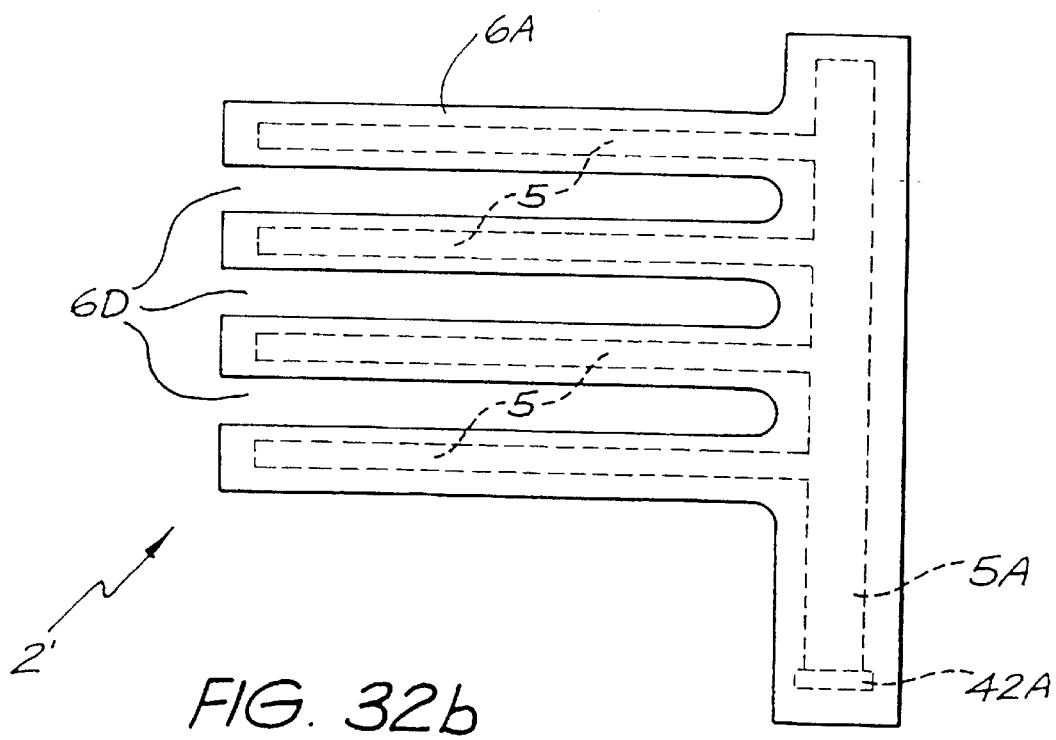

In a further simplification to the above-mentioned design for increased patient comfort, the sensor strips 5 may be enclosed by the waterproof envelope 6A only in the immediate vicinity thereof (FIG. 32b). In this configuration gaps 6D between the enclosed sensor strips 5 facilitate the above-mentioned diffusion of humidity away from the subject.

Figure 32C:
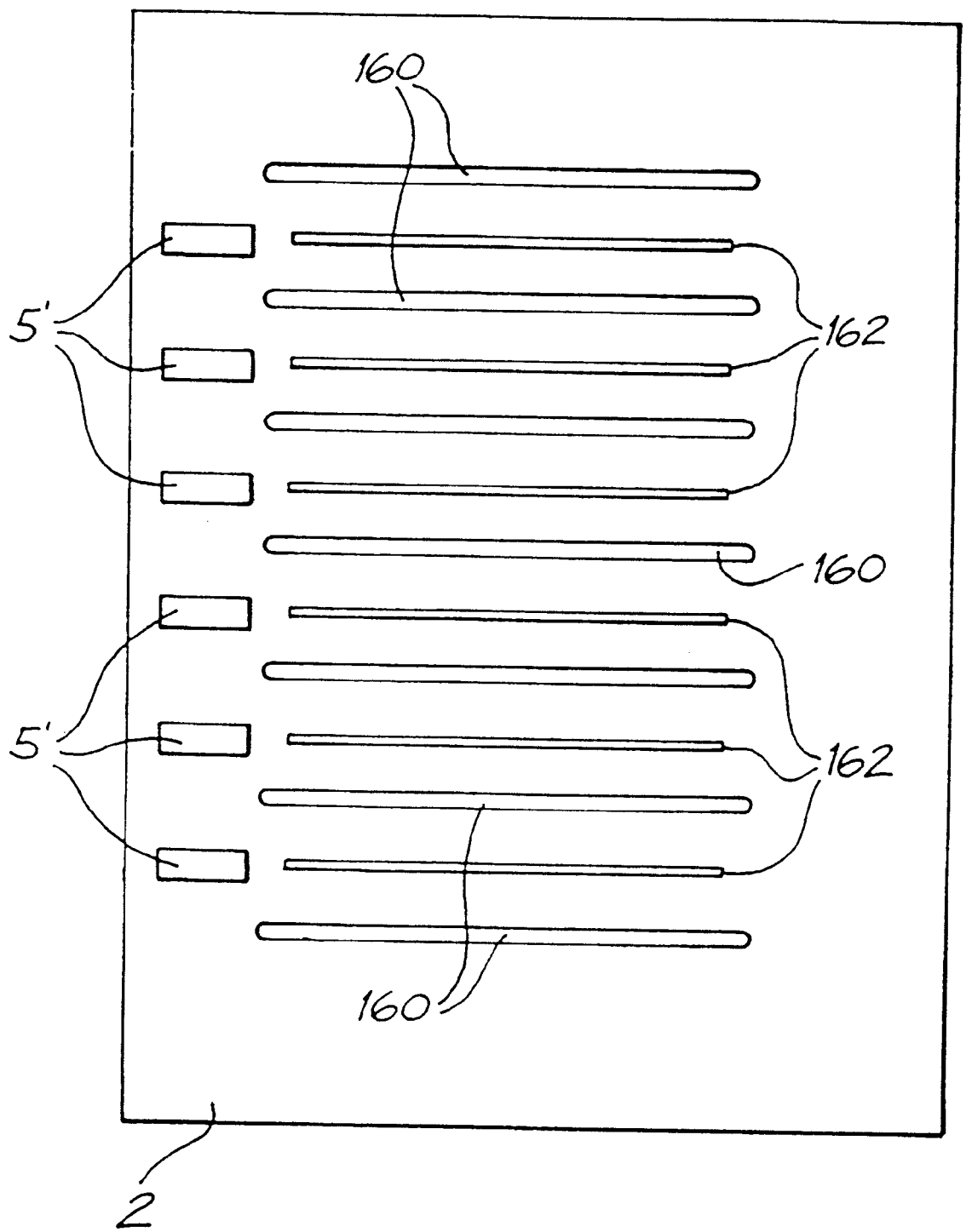

FIG. 32c shows an arrangement of six sensors 5' arranged at the edge margin of the mattress 2. Lateral strain elements 162, acting to channel vertical body displacement to the respective sensor 5' are provided. If preferred, a series of alternating slits 160 can be provided to decouple or isolate adjacent strain elements 162. In another form, channelling of the lateral strain to each sensor 5' may be achieved by use of a substrate material (not shown) in which the lateral (left-to-right) stiffness is significantly greater than the longitudinal (head-to-toe) direction.

Figure 33:
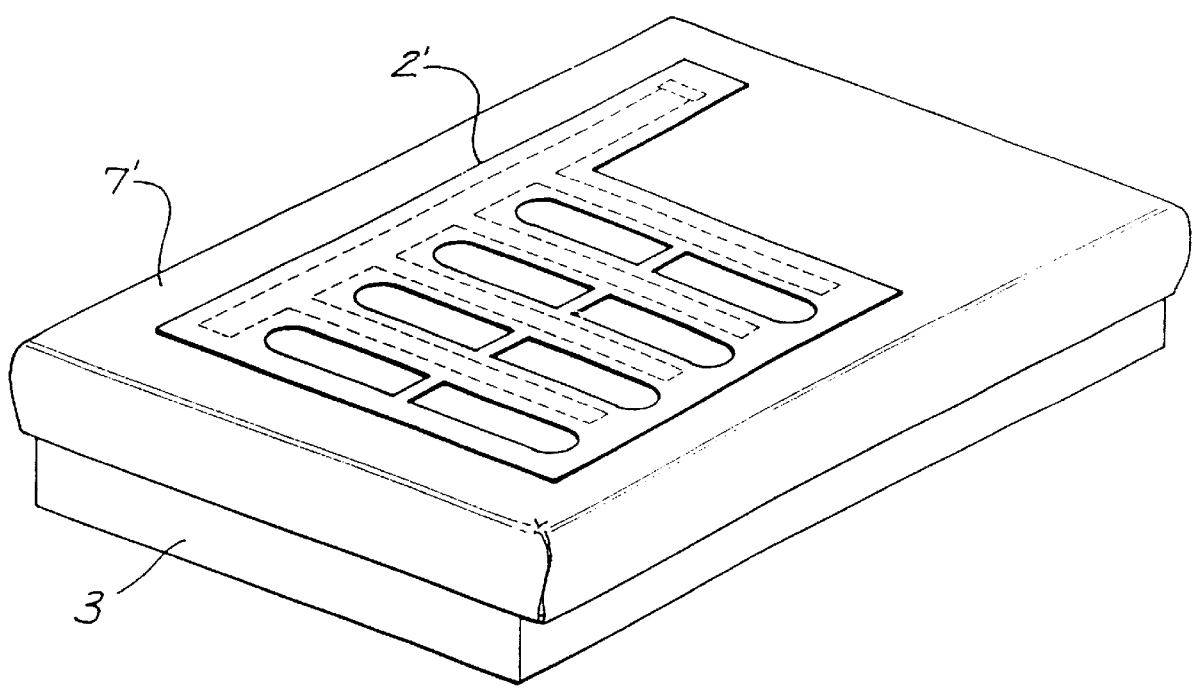
FIG. 33 shows the movement-sensitive sheet of FIG. 32a mounted on a carrier sheet, which can be in the form of a conventional fitted sheet.

In another implementation which improves the ability to locate accurately the sensor strips 5 and aids subject comfort, the movement-sensitive mattress or sheet 2' is mounted on a carrier sheet 7' typically made of cotton or an equivalent porous bed sheeting material or net (FIG. 33). The mounting method for the construction may be permanent, whereby movement-sensitive mattress or sheet 2' is permanently bounded to carrier sheet 7', or removable, whereby movement-sensitive mattress or sheet 2' is attached to carrier sheet 7' by fastenings such as haberdashers' press studs or "VELCRO"™ hook and loop material. The construction of carrier sheet 7' can, advantageously, follow the form of a conventional "fitted" bedding sheet whereby an elasticated border (not shown) holds the carrier sheet 7' on a conventional mattress 3.

What is claimed is:

1. A mattress for monitoring patient movement for a patient lying on the mattress, the mattress including a plurality of independent, like movement sensors for measuring movement at different locations on the mattress to generate a plurality of independent movement signals each configured to be processed independently of the remaining independent movement signals.

2. A mattress as claimed in claim 1, wherein the number of movement sensors is in the range three to ten.

3. A mattress as claimed in claim 1, wherein the movement sensors are formed by piezoelectric elements.

4. A mattress as claimed in claim 3, wherein said elements are fabricated from polyvinylidene fluoride (PVDF) material.

5. A mattress as claimed in claim 3, wherein at least some of the elements are arranged to measure lateral strain across the mattress.

6. A mattress as claimed in claim 3, further comprising compressible filling surrounded by an outer layer, and wherein said elements are attached to an inner surface of the outer layer.

7. A mattress as claimed in claim 3, wherein the elements are laminated between two thin conformable elastic sheets.

8. A mattress as claimed in claim 3, further comprising a separate transition connector connected to each of said elements in such a manner as to avoid strain between the strip and each said connector during use of the mattress.

9. A mattress as claimed in claim 3, further comprising a single bus transition connector to which each of the elements is connected.

10. A mattress as claimed in claim 3, wherein said elements are integrally formed from a single composite sheet of piezoelectric material by forming a series of staggered parallel cuts in said sheet in such a way that each of the elements is formed between two adjacent cuts.

11. A respiratory analysis system for monitoring at least one respiratory variable for a patient, the system comprising:
    a mattress upon which the patient can lie, having a plurality of independent, like movement sensors for measuring movement at different locations on the mattress to generate a plurality of independent movement signals; and
    a processor to receive and process said movement signals to derive said at least one respiratory variable.

12. A system as claimed in claim 11, wherein the processor is programmed to bandpass filter the movement signals, and to correlate a spatial distribution of the filtered signals at a given time with a spatial distribution of an earlier time to produce a respiratory rate as said at least one respiratory variable.

13. A system claimed in claim 12, wherein the processor is programmed to detect a change in respiratory phase by monitoring a value of the earlier time correlation of the spatial distribution of the filtered signals, and detects a change in respiratory phase when the processor detects a reduction of duration of signal matching as indicative of a change in respiratory phase, said reduction of duration being a further said at least one respiratory variable.

14. A system as claimed in claim 13, wherein the processor is further programmed to determine an elapsed time between a last two respiratory phase changes as indicative of respiratory rate, said elapsed time being a further said at least one respiratory variable.

15. A system as claimed in claim 12, wherein the processor is programmed to derive a diagnostic variable from said at least one respiratory variable.

16. A system as claimed in claim 11, wherein the processor is programmed to bandpass filter the movement signals, and to correlate a spatial distribution of the filtered signals at a given time with a spatial distribution of an earlier time to produce a heartrate as said at least one respiratory variable.

17. A system as claimed in claim 11, wherein the processor is programmed to bandpass filter at least one of the movement signals, take a modulus of the at least one filtered signal, low pass filters each said modulus signal, and at least one of (i) average and (ii) measure a maximum output of each said low pass filtered signal over one of an entire duration of each breath and each phase separately to give respiratory effort as said at least one respiratory variable.

18. A system claimed in claim 11, further comprising a pre-processor to receive said movement signals, pre-process the movement signals by one of equalizing each of the movement signals and deconvolving spatially the movement signals, and pass said pre-processed signals to said processor.

19. A system as claimed in claim 11, further including an output device for outputting said at least one respiratory variable.

20. A system as claimed in claim 11, further including a storage device for storing said at least one respiratory variable.

21. A method for monitoring at least one respiratory variable for a patient lying on a mattress, the method comprising:
  measuring displacement due to body movement at a plurality of independent positions length-wise of a portion of the body to derive independent signals representative of respective individual body displacement at said positions; and
  processing said movement signals to derive said at least one respiratory variable.

22. A method as claimed in claim 21, further comprising deriving a diagnostic variable from said at least one respiratory variable.

23. A method as claimed in claim 21, further comprising pre-processing said movement signals by one of equalization and spatial deconvolution before performing said processing.

24. A respiratory analysis system for monitoring at least one respiratory variable of a patient, comprising an input device to receive a plurality of signals indicative of patient movement; and a processor to process said received signals to derive said at least one respiratory variable.

25. A system as claimed in claim 24, wherein the processor is programmed to bandpass filter the movement signals, and correlate a spatial distribution of the filtered signals at a given time with a spatial distribution of an earlier time to produce a respiratory rate as said at least one respiratory variable.

26. A system as claimed in claim 25, wherein the processor is programmed to monitor a value of the earlier time correlation of the spatial distribution of the filtered signals, and detects a reduction of duration of signal matching as indicative of a change in respiratory phase, said reduction of duration being a further said at least one respiratory variable.

27. A system as claimed in claim 26, wherein the processor is further programmed to determined an elapsed time between a last two respiratory phase changes as indicative of respiratory rate, said elapsed time being a further said at least one respiratory variable.

28. A system as claimed in claim 25, wherein the processor is further programmed to derive a diagnostic variable from said at least one respiratory variable.

29. A system as claimed in claim 24, wherein the processor is programmed to bandpass filter the movement signals, and correlate a spatial distribution of the filtered signals at a given time with a spatial distribution of an earlier time to produce a respiratory rate as said at least one respiratory variable.

30. A system claimed in claim 24, wherein the processor is programmed to bandpass filter at least one of the movement signals, take a modulus of the at least one filtered signal, low pass filter each said modulus signal, and at least one of (i) average and (ii) measure a maximum output of each said low pass filtered signal over one of an entire duration of each breath and each phase separately to give respiratory effort as said at least one respiratory variable.

31. A system as claimed in claim 24, further comprising a pre-processor to receive said movement signals, pre-process the movement signals by one of equalizing each movement signal and deconvolving spacially the movement signals, and pass said pre-processed signals to said processor.

32. A system as claimed in claim 24, further including an output device for outputting said at least one respiratory variable.

33. A system or method as claimed in claim 11, further wherein said at least one respiratory variable is used to control the output treatment pressure of a CPAP device.

34. A system or method as claimed in claim 11, wherein said at least one respiratory variable is used to monitor one of CPAP treatment effectiveness and, patient compliance.

35. A system as claimed in claim 24, further including a storage device for storing said at least one respiratory variable.

36. A respiratory analysis system for monitoring at least one respiratory variable of a patient, the system comprising:
  a mattress upon which the patient can lie and having a plurality of independent movement sensors for measuring movement at different locations on the mattress to generate a plurality of independent movement signals; and
  a processor to receive and process said movement signals to derive said at least one respiratory variable.

37. A mattress for monitoring patient movement for a patient lying on the mattress, the mattress including a plurality of independent movement sensors for measuring movement at different locations on the mattress to generate a plurality of independent movement signals each configured for independent processing.

38. A method for monitoring patient movement for a patient lying on a mattress, the method comprising measuring displacement due to body movement at a plurality of independent positions length-wise of a portion of the body to derive independent signals representative of respective individual body displacement at said positions.

39. A method as claimed in claim 38, wherein each of the independent signals is configured for independent processing.

* * * * *